US011304648B2

(12) United States Patent
Rondoni et al.

(10) Patent No.: US 11,304,648 B2
(45) Date of Patent: Apr. 19, 2022

(54) METHOD AND SYSTEM FOR IDENTIFYING A LOCATION FOR NERVE STIMULATION

(71) Applicant: INSPIRE MEDICAL SYSTEMS, INC., Maple Grove, MN (US)

(72) Inventors: John Rondoni, Maple Grove, MN (US); Mark A. Christopherson, Maple Grove, MN (US); Quan Ni, Maple Grove, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 439 days.

(21) Appl. No.: 15/894,494

(22) Filed: Feb. 12, 2018

(65) Prior Publication Data
US 2018/0220921 A1    Aug. 9, 2018

Related U.S. Application Data

(63) Continuation of application No. 13/634,333, filed as application No. PCT/US2011/027956 on Mar. 10, 2011, now Pat. No. 9,888,864.
(Continued)

(51) Int. Cl.
*A61B 5/389* (2021.01)
*A61B 5/11* (2006.01)
(Continued)

(52) U.S. Cl.
CPC ............ *A61B 5/389* (2021.01); *A61B 5/0536* (2013.01); *A61B 5/08* (2013.01); *A61B 5/1104* (2013.01);
(Continued)

(58) Field of Classification Search
CPC ..... A61B 5/0536; A61B 5/08; A61B 5/04001; A61B 5/4893; A61B 5/1104;
(Continued)

(56) References Cited

U.S. PATENT DOCUMENTS 4,485,815 A   12/1984  Amplatz
5,158,080 A   10/1992  Kallok
(Continued)

FOREIGN PATENT DOCUMENTS

EP    0743076 A1    11/1996
SU    925349         5/1992
(Continued)

OTHER PUBLICATIONS

Mann Article—Eric A. Mann, MD, PhD et al., "The Effect of Neuromuscular Stimulation of the Genioglossus on the Hypopharyngeal Airway," The American Laryngouogical, Rhinological and Otological Society, Inc., 2002, pp. 351-356.
(Continued)

*Primary Examiner* — Thomas McEvoy
(74) *Attorney, Agent, or Firm* — Dicke, Billig & Czaja, PLLC

(57) ABSTRACT

A system and method for identifying a stimulation location on a nerve is disclosed. The system includes an image-based navigation interface used to facilitate advancing a stimulation element within a patient body toward a target nerve stimulation site. Using the system one determines, separately for each potential target nerve stimulation site, a neuromuscular response of muscles produced upon applying a stimulation signal at the respective separate potential target stimulation sites. The image-based navigation interface is configured to display a graphic identification of which muscles were activated for each respective potential target nerve stimulation site upon applying the stimulation signal.

16 Claims, 10 Drawing Sheets

Related U.S. Application Data

(60) Provisional application No. 61/313,406, filed on Mar. 12, 2010.

(51) Int. Cl.

| | | |
|---|---|---|
| *A61B 5/00* | (2006.01) | |
| *A61N 1/372* | (2006.01) | |
| *A61B 34/20* | (2016.01) | |
| *A61B 5/24* | (2021.01) | |
| *A61B 5/0536* | (2021.01) | |
| *A61B 5/08* | (2006.01) | |
| *A61B 34/00* | (2016.01) | |

(52) U.S. Cl.
CPC .............. *A61B 5/24* (2021.01); *A61B 5/4519* (2013.01); *A61B 5/4818* (2013.01); *A61B 5/4893* (2013.01); *A61B 5/6814* (2013.01); *A61B 5/6822* (2013.01); *A61B 34/20* (2016.02); *A61N 1/372* (2013.01); *A61B 5/682* (2013.01); *A61B 5/6839* (2013.01); *A61B 5/6843* (2013.01); *A61B 5/6849* (2013.01); *A61B 5/7425* (2013.01); *A61B 5/7435* (2013.01); *A61B 34/25* (2016.02); *A61B 2034/2065* (2016.02); *A61B 2505/05* (2013.01); *A61B 2562/043* (2013.01); *A61N 1/37241* (2013.01); *A61N 1/37247* (2013.01)

(58) Field of Classification Search
CPC ... A61B 5/4519; A61B 5/4818; A61B 5/6814; A61B 5/6822; A61B 34/20; A61B 5/682; A61B 5/6839; A61B 5/6843; A61B 5/6849; A61B 5/7425; A61B 5/7435; A61B 34/25; A61B 2034/2065; A61B 2505/05; A61B 2562/043; A61N 1/372; A61N 1/37241; A61N 1/37247

See application file for complete search history.

(56) References Cited

U.S. PATENT DOCUMENTS

| | | | |
|---|---|---|---|
| 5,190,053 A | 3/1993 | Meer | |
| 5,226,427 A | 7/1993 | Buckberg | |
| 5,230,338 A | 7/1993 | Allen | |
| 5,344,438 A | 9/1994 | Testerman et al. | |
| 5,560,372 A | 10/1996 | Cory | |
| 5,591,216 A | 1/1997 | Testerman et al. | |
| 6,065,154 A | 5/2000 | Hulings et al. | |
| 6,181,961 B1 | 1/2001 | Prass | |
| 6,361,494 B1 | 3/2002 | Lindenthaler | |
| 6,449,507 B1 | 9/2002 | Hill et al. | |
| 6,456,866 B1 | 9/2002 | Durand et al. | |
| 6,535,759 B1 | 3/2003 | Epstein et al. | |
| 6,587,725 B1 | 7/2003 | Durand et al. | |
| 6,609,032 B1 | 8/2003 | Woods et al. | |
| 6,654,634 B1 | 11/2003 | Prass | |
| 6,718,208 B2 | 4/2004 | Hill et al. | |
| 7,104,965 B1 | 9/2006 | Jiang et al. | |
| 7,160,255 B2 | 1/2007 | Saadat | |
| 7,214,197 B2 | 5/2007 | Prass | |
| 7,216,000 B2 | 5/2007 | Sieracki et al. | |
| 7,277,749 B2 | 10/2007 | Gordon | |
| 7,366,562 B2 | 4/2008 | Dukesherer | |
| 7,599,730 B2 | 10/2009 | Hunter | |
| 7,606,613 B2 | 10/2009 | Simon | |
| 7,644,714 B2 | 1/2010 | Atkinson et al. | |
| 7,657,308 B2 | 2/2010 | Miles et al. | |
| 7,680,538 B2 | 3/2010 | Durand et al. | |
| 7,725,195 B2 | 5/2010 | Lima et al. | |
| 7,809,442 B2 | 10/2010 | Bolea et al. | |
| 9,888,864 B2 | 2/2018 | Rondoni et al. | |
| 2001/0010010 A1 | 7/2001 | Richmond et al. | |
| 2002/0010495 A1 | 1/2002 | Freed et al. | |
| 2002/0049479 A1 | 4/2002 | Pitts | |
| 2002/0120188 A1 | 8/2002 | Brock | |
| 2003/0093128 A1 | 5/2003 | Freed et al. | |
| 2004/0015204 A1 | 1/2004 | Whitehurst et al. | |
| 2004/0073272 A1 | 4/2004 | Knudson et al. | |
| 2004/0116819 A1 | 6/2004 | Alt | |
| 2004/0260310 A1 | 12/2004 | Harris | |
| 2005/0234431 A1* | 10/2005 | Williams | A61M 25/04 604/890.1 |
| 2005/0267547 A1 | 12/2005 | Knudson | |
| 2006/0103407 A1 | 5/2006 | Kakizawa et al. | |
| 2006/0266369 A1 | 11/2006 | Atkinson et al. | |
| 2007/0233204 A1 | 10/2007 | Lima et al. | |
| 2007/0255379 A1 | 11/2007 | Williams et al. | |
| 2008/0046055 A1 | 2/2008 | Durand et al. | |
| 2008/0064977 A1 | 3/2008 | Kelleher et al. | |
| 2008/0097187 A1 | 4/2008 | Gielen | |
| 2008/0103407 A1* | 5/2008 | Bolea | A61N 1/37229 600/529 |
| 2008/0103545 A1 | 5/2008 | Bolea et al. | |
| 2008/0139930 A1 | 6/2008 | Weese | |
| 2008/0172101 A1 | 7/2008 | Bolea et al. | |
| 2008/0177348 A1 | 7/2008 | Bolea et al. | |
| 2008/0208282 A1 | 8/2008 | Gelfand et al. | |
| 2008/0269602 A1 | 10/2008 | Csavoy | |
| 2009/0187124 A1 | 7/2009 | Ludlow et al. | |
| 2009/0209879 A1 | 8/2009 | Kaula et al. | |
| 2009/0308395 A1 | 12/2009 | Lee | |
| 2010/0010367 A1 | 1/2010 | Foley et al. | |
| 2010/0036285 A1 | 2/2010 | Govari | |
| 2010/0094379 A1 | 4/2010 | Meadows | |
| 2010/0174341 A1 | 7/2010 | Bolea et al. | |
| 2010/0198103 A1 | 8/2010 | Meadows et al. | |
| 2010/0241195 A1 | 9/2010 | Meadows et al. | |
| 2011/0093036 A1 | 4/2011 | Mashiach | |
| 2011/0152965 A1 | 6/2011 | Mashiach | |

FOREIGN PATENT DOCUMENTS

| | | |
|---|---|---|
| WO | 2003026482 | 4/2003 |
| WO | 2004064634 | 8/2004 |
| WO | 2005013805 | 2/2005 |
| WO | 2008048471 | 4/2008 |
| WO | 2009048580 | 4/2009 |
| WO | 2009048581 | 4/2009 |
| WO | 2009135075 | 11/2009 |
| WO | 2009135138 | 11/2009 |
| WO | 2009135140 | 11/2009 |
| WO | 2009135142 | 11/2009 |
| WO | 2009140636 | 11/2009 |
| WO | 2010014260 | 2/2010 |
| WO | 2010039853 | 4/2010 |
| WO | 2010059839 | 5/2010 |
| WO | 2010117810 | 10/2010 |
| WO | 2011112843 | 9/2011 |

OTHER PUBLICATIONS

Park Article—Jung I. Park MD, PhD, "Preoperative Percutaneous Cranial Nerve Mapping in Head and Neck Surgery", American Medical Association, 2003, (6 pages).

Medtronic, "Navigation Tracking Technologies", Medtronic website, Dec. 28, 2008, 1 page.

Van Buyten, et al., "Percutaneous technique for the treatment of Trigeminal Neuralgia becomes more precise and safer with the use of new Electromagnetic (EM) Navigation Technology", Nov. 1994, 6 pages.

Medtronic, "Intracardiac Navigation System", Medtronic website, Dec. 17, 2009, 2 pages.

Medtronic, "The O-ARM Imaging System", Medtronic website, Dec. 28, 2008, 1 page.

Medtronic, Stealth Station S7, "See the Bigger Picture", Medtronic website, Apr. 2008, 2 pages.

* cited by examiner

METHOD AND SYSTEM FOR IDENTIFYING A LOCATION FOR NERVE STIMULATION

CROSS-REFERENCE TO RELATED APPLICATIONS

This Utility Patent Application is a Continuation of U.S. patent application Ser. No. 13/634,333, which entered the U.S. National Phase on Oct. 22, 2012, entitled "METHOD AND SYSTEM FOR IDENTIFYING A LOCATION FOR NERVE STIMULATION", and which claims benefit of PCT Application PCT/US11/027956, filed Mar. 10, 2011, entitled "METHOD AND SYSTEM FOR IDENTIFYING A LOCATION FOR NERVE STIMULATION" and which claims benefit of Provisional Application 61/313,406, filed Mar. 12, 2010, entitled "METHOD AND SYSTEM FOR IDENTIFYING A LOCATION FOR NERVE STIMULATION" all of which are incorporated herein by reference.

BACKGROUND

Advanced imaging techniques, such as magnetic resonance imaging (MRI), have revolutionized diagnosis and treatment of various patient maladies. In particular, such techniques permit observation of internal structures, such as soft tissues, that were previously unidentifiable in traditional radiographic techniques (such as X-ray). As such, a wide variety of internal organs, tissues, connective tissue is now viewable along with the previously viewable bony structures. Using the MRI or other advanced imaging techniques (such as computer tomography, CT), physicians can readily diagnosis or exclude many conditions.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF THE EMBODIMENTS

The following detailed description is merely exemplary in nature and is not intended to limit the present general inventive concept or the application and uses of the present general inventive concept. Furthermore, there is no intention to be bound by any expressed or implied theory presented in the preceding technical field, background, or the following detailed description.

Embodiments of the present general inventive concept are directed to enhancing surgical navigation via combining, in a graphical user interface, image-based visualization of the soft and hard tissues of a relevant body region simultaneous with graphical representation (within the image-based visualization) of muscle activation from a stimulation signal applied at a target site. In some embodiments, in concert with visualization of a stimulation element within the image-based navigation interface, a stimulation path analyzer makes a quantitative evaluation of muscle responses from nerve stimulation to determine a precise location of the stimulation element relative to pertinent soft tissues (such as muscles, nerves, and major circulatory vessels) and also relative to bony structures, which serve as reference points. With this combination, one can determine and visually represent a location of a stimulation element in a body region in real time using image-navigation tools simultaneous with functional evaluation of the electrode placement (e.g. does the tongue protrude upon stimulation from the stimulation element? is the proper muscle group activated?) and simultaneous with quantitative evaluation of the stimulation location, such as nerve conduction and muscle response information (e.g. electromyography and/or compound muscle action potential).

In some embodiments, the quantitative evaluation information of which muscle is activated is expressed within the image-based navigation interface via highlighting a graphical representation of the activated muscle among other muscles and anatomical structures. In one embodiment, the system differentiates between target muscles and non-target muscles in the image-based navigation interface via color, shading, and/or other patterns. Accordingly, the system greatly simplifies the role of an operator by providing real-time representations of the effect of a particular location of a stimulation element. In one embodiment, this arrangement is of particular benefit to facilitate percutaneous placement of an implantable nerve stimulation electrode usable in a method of treating obstructive sleep apnea or other sleep-breathing disorders.

These embodiments, and additional embodiments, are described in more detail in association with FIGS. 1-14 of the present general inventive concept.

Figure 1:
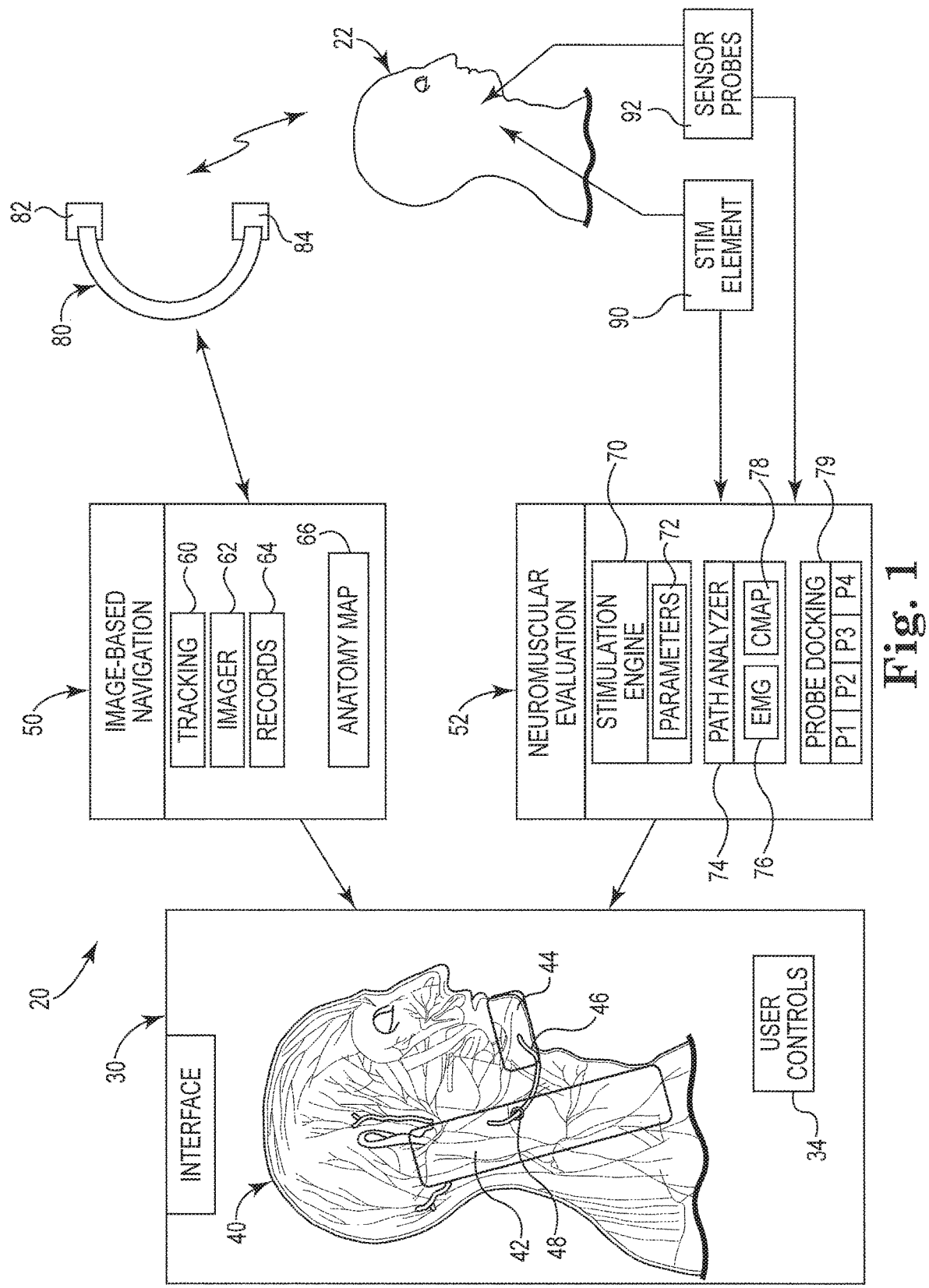
FIG. 1 is a schematic illustration of a system and method for navigation via images and via neuromuscular responses from stimulation, according to an embodiment of the present general inventive concept.

FIG. 1 is diagram schematically illustrating a system and method for navigation via images and via neuromuscular responses from electrical stimulation, according to an embodiment of the present general inventive concept. In one embodiment, system 20 has particular application to facilitate a minimally invasive, percutaneous or transvenous placement of an implantable nerve stimulation electrode and thereby avoid a traditional, highly invasive cut-down access procedure.

As illustrated by FIG. 1, system 20 includes interface 30, image-based navigation module 50, and neuromuscular response evaluator 52. In general terms, interface 30 includes a graphical user interface configured to simultaneously display images and neuromuscular responses in an integrated manner. User controls 34 enable a user to operate and control at least some functions of image-based navigation module 50, parameters of interface 30, and/or neuromuscular response evaluator 52. In some embodiments, on screen controls would be supplemented by one or more additional control mechanisms, such as foot pedals, voice recognition commands, a sterilized navi-pad.

In one embodiment, user controls 34 include laser projection onto the patient and/or onto tissues for identifying anatomical features, landmarks, and distances. In some embodiments, multiple lasers (each having a different color) are used to help differentiate between multiple anatomical features, landmarks, and distances, as further described later in association with at least FIGS. 10 and 14.

As illustrated by FIG. 1, interface 30 displays an image 40 of relevant anatomical features of a body portion of patient 22. In addition, as further described below, superimposed on the image 40 are muscle identifiers 42, 44 and a nerve identifier 46, which together indicate which nerve is being stimulated, where is it being stimulated, and which muscles are activated as a result. In one aspect, nerve identifier 46 is operable to separately identify multiple nerves to differentiate within interface 30 each respective nerve, as well as differentiating identification of relevant branches of a nerve. In some embodiments, interface 30 additionally indicates a target nerve and a target muscle innervated by the target nerve, such that interface 30 enables confirmation of whether the target muscle or a different muscle has been activated via stimulation of a nerve, as will be further described later in association with FIGS. 4-11.

In one embodiment, the image-based navigation module 50 includes a tracking function 60, an imager function 62, a records function 64, and an anatomy map function 66.

In general terms, the imager function 62 obtains and/provides images of a body portion of patient 22. In some embodiments, the image is obtained via an imaging system 80 (not shown to scale for illustrative purposes) including a transmitter 82 and receiver 84, which function together to capture internal images of patient 22. The imaging system 80 includes, but is not limited to, any one of a magnetic resonance imager (MRI), computer tomography (CT) unit, fluoroscopic imager, endoscopy, etc., or combinations thereof, as is further illustrated in FIG. 3. In one example, endoscopy is used to observe evoked responses.

Figure 3:
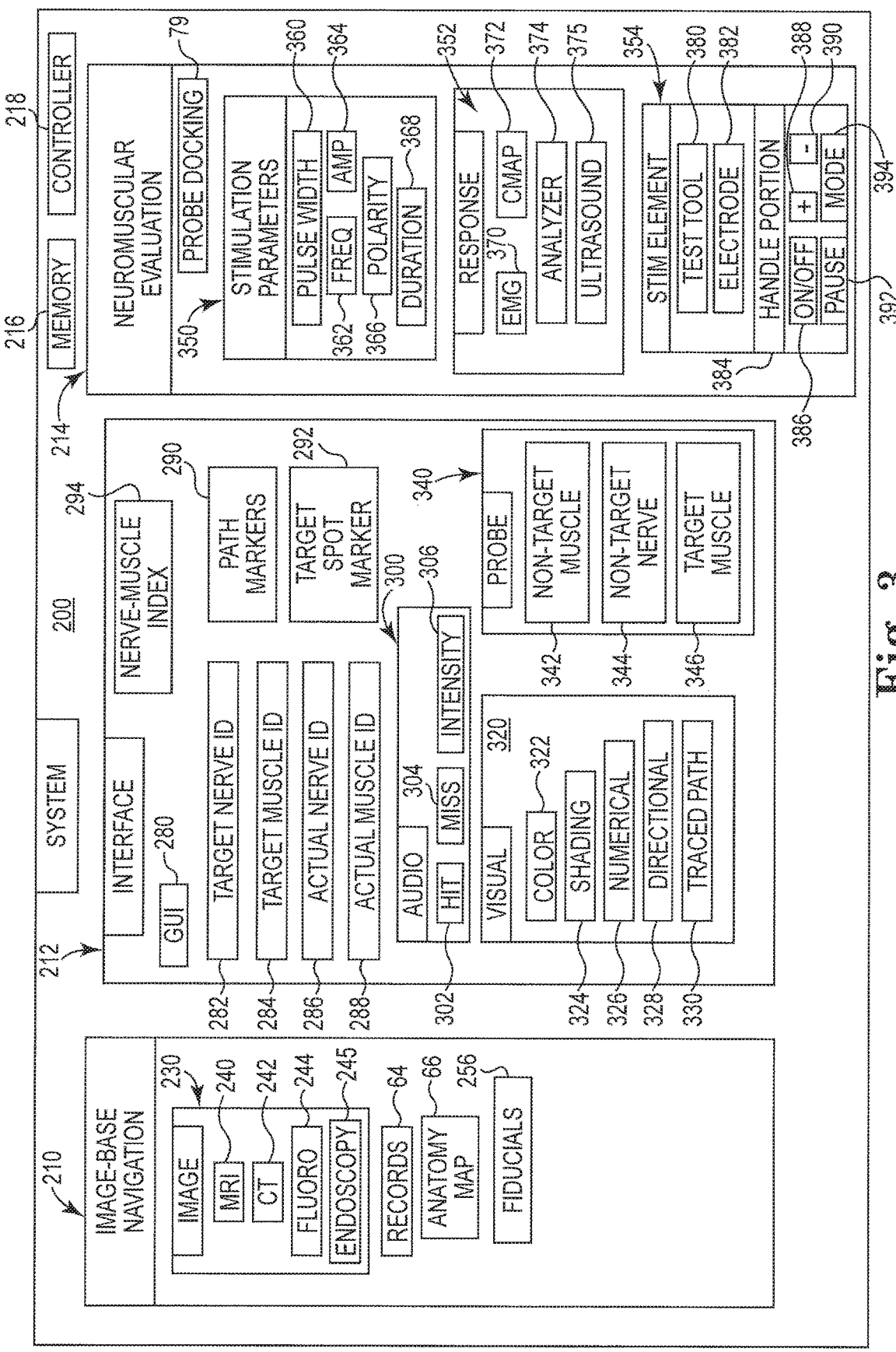
FIG. 3 is a block diagram of a system for navigation, according to an embodiment of the present general inventive concept.

Records function 64 of image-based navigation module 50 enables access to one or more stored image records of patient 22, via an electronic medical records (EMR) system or other resources as further noted in association with FIG. 3. Anatomy map function 66 enables access to general anatomical maps and images, suitably scaled, to overlay or superimpose relative to obtained images of patient 22. In some embodiments, a patient-specific image (such as CT or MRI), is overlaid onto, and synchronized relative to, a generalized anatomy map using commercially available image analysis techniques, such as those provided via Vital Images, Inc. of Minnetonka, Minn. The patient-specific images are obtained via known systems such as electronic medical records (EMR) and/or a picture archiving communication system (PACS). In some embodiments, the images are obtained and/or communicated according to a Health Level 7 standard for electronic medical records.

In this way, a generally comprehensive picture of relevant anatomical features of a body portion of patient 22 are provided in interface 30 (FIG. 1) to facilitate identifying target nerves and muscles when locating a target stimulation site for an electrode (or electrode array) and when mapping a percutaneous access pathway to that target stimulation site.

By utilizing imager function 62, records function 64 and/or anatomy map function 66, the tracking function 60 enables visually tracking (via interface 30) a location of stimulation element 90 and/or support instruments used to guide and place stimulation element 90. In some embodiments, the stimulation element 90 is a stimulation test tool while in other embodiments, the stimulation element 90 is an implantable electrode.

In one embodiment, as shown in FIG. 1, the relevant body region of patient 22 displayed in interface 30 includes an upper respiratory system including the mouth to enable visualizing the tongue, its underlying and surrounding muscle groups, related nerve pathways, and supporting bony structures. In some embodiments, visualization of these detailed structures (and their interrelationship) is used to treat sleep-disordered breathing, such as obstructive sleep apnea.

In general terms, the neuromuscular response evaluator 52 of system 20 (FIG. 1) is configured to apply a stimulation signal through stimulation element 90 via a stimulation engine 70 according to stimulation parameters 72. The produced neuromuscular response is sensed with probes 92 (for example, probes shown in FIGS. 7-9) and fed to a stimulation path analyzer 74. Via an electromyography function 76 and a compound muscle action potential function (CMAP) 78, the stimulation path analyzer 74 differentiates whether the activation of the muscle occurred because of stimulation of a nerve innervating that activated muscle or because of direct electrical stimulation of the activated muscle. In some embodiments, at least some of the functions of the response evaluator 52 are provided via a nerve integrity monitor. In this regard, in one embodiment, the nerve integrity monitor comprises at least substantially the same features and attributes as the nerve integrity monitor described in U.S. Pat. No. 6,334,068, entitled INTRAOPERATIVE NEUROELECTROPHYSIOLOGICAL MONITOR, issued on Dec. 25, 2001, and which is hereby incorporated by reference in its entirety. In other embodiments, other commercially available nerve integrity monitors or an equivalent array of instruments (e.g., a stimulation probe and electromyography system) are used to apply the stimulation signal and evaluate the response of the muscle innervated by the target nerve.

In some embodiments, a plurality of sensor probes is placed at and near muscles to be activated. In one embodiment, the sensor probes comprise fine wire needle electrode typically used in nerve integrity monitoring. With the sensor probes in place and using interface 30, one can observe which muscles are activated upon stimulation of the different sites and via path analyzer 74, one can systematically reveal which stimulation site will result in activation of the desired muscle. This arrangement is described further in association with FIGS. 6A-6B. Accordingly, in some embodiments, system 20 includes a probe docking module 79 to establish electrical communication between the sensor probes 92, neuromuscular response evaluator 52, and interface 30. Via programming, the probe docking module 79 associates each separate probe 92 with a specific muscle of the patient 22 so that when the muscle associated with a particular probe is activated, the interface 30 can visually highlight that muscle on the displayed image 40. For example, highlighted region 42 of image 40 is associated with probe P2 while highlighted region 44 of image 40 is associated with probe P1. In this way, the interface 30 correlates the location of the sensor probes 92 with the anatomical features of the patient 22 in the displayed image 40. In some embodiments, this arrangement is facilitated via a nerve-muscle index 294, which is further described later in association with FIGS. 3 and 6B.

In some embodiments, the stimulation element 90 includes a stimulation test tool configured to be inserted percutaneously into a body of patient 22 to releasably engage a potential stimulation site and enable a stimulation signal to be applied at that site, such as a target nerve. In other embodiments, the stimulation element 90 includes a cuff electrode (or other electrode configuration) configured to be implanted in a secured relationship relative to a target stimulation site of a nerve in order to provide long-term implantable stimulation therapy via activation of an innervated muscle. For example, in one embodiment, the target nerve is a hypoglossal nerve and the innervated muscle is the genioglossus muscle. In some embodiments, the target nerve is a particular branch (or branches) of the hypoglossal nerve. For example, in one example the target nerve includes one or more particular lateral branches or medial branch of the hypoglossal nerve, such that the innervated muscle includes the styloglossus muscle, the hyoglossus muscles, the geniohyoid muscle, and/or the genioglossus muscle.

In one instance, the cuff electrode is delivered to the target stimulation site of the nerve via minimally invasive, percutaneous access (which avoids the more traditional, highly invasive cut-down access procedure). As more fully described herein, such percutaneous access for cuff electrode is guided via both the image-based navigation module 50 and neuromuscular response evaluator 52. In one embodiment, one such percutaneous access method is described and illustrated in application Ser. No. 61/165,110, filed Mar. 31, 2009, and titled PERCUTANEOUS ACCESS METHOD AND SURGICAL NAVIGATION TECHNIQUES. It will be understood that in some embodiments, other minimally invasive methods, such as microendoscopic delivery techniques, are used to place the implantable cuff electrode in cooperation with the guidance of the image-based navigation module 50 and neuromuscular response evaluator 52.

In yet other embodiments, transvenous access delivery methods of a stimulation electrode are used to place the stimulation electrode at a target stimulation site relative to target nerve, and that even this transvenous delivery is aided or guided via image-based navigation module 50 and neuromuscular response evaluator 52 in accordance with principles of the present general inventive concept, or in accordance with other imaging techniques. In one embodiment, one such transvenous access method is described and illustrated in co-pending PCT application serial number PCT/US2009/059060, filed Sep. 30, 2009, and titled TRANSVENOUS METHOD OF TREATING SLEEP APNEA.

With this arrangement in mind, the produced neuromuscular responses are visually represented on interface 30 via a highlighted portion of image 40, such as via color highlighting or shading. As shown in FIG. 1, the highlighted portions can take particular shapes and sizes, such as rectangular shapes, that may or may not approximate the general shape and size of a subject's anatomical features. In some embodiments, the location, size, and/or shape of the highlightable portions of interface 40 (such as the colored or shaded portions corresponding to a particular anatomical feature) is established at the time that sensor probes are placed relative to the patient's anatomy.

In the non-limiting example illustrated by FIG. 1, a highlighted portion 42 of interface 30 corresponds to a deduced location of an activated muscle (i.e., the muscle actually activated, associated with probe P2) while a highlighted portion 44 (associated with probe P1) corresponds to a target muscle that is desired to be activated. Identifier 48 highlights the location at which stimulation takes place on nerve 46. Moreover, as the system 10 tracks the real-time location of the stimulation element 90, the location of the stimulation element 90 is dynamically represented via identifier 48 as part of displayed image 40.

With this arrangement, interface 30 simultaneously combines the image-based navigation information with the neuromuscular response information to provide a real-time indication of which muscles are activated via stimulation (and to what degree) and a real-time indication of the location of the stimulation element causing the muscle activation. Using this information, interface 30 assists a physician in maneuvering the stimulation element to a target stimulation site for an innervated muscle to be activated via stimulation.

Figure 2:
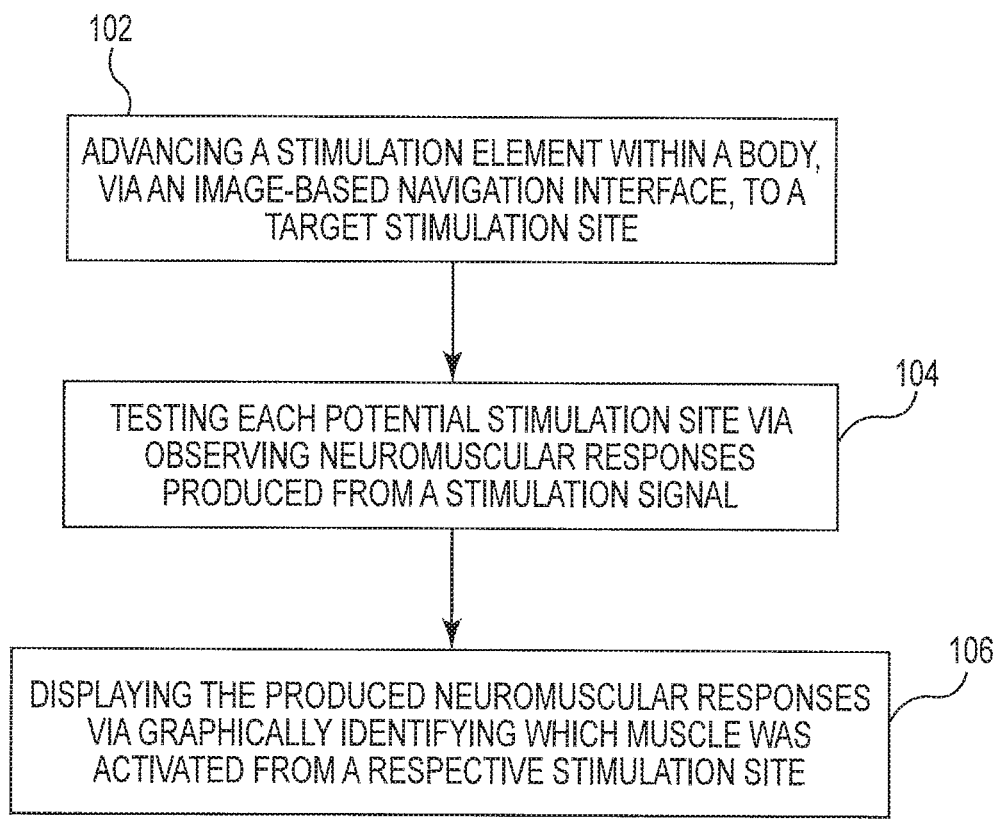
FIG. 2 is a flow diagram of a method of navigating placement of a stimulation element within a body, according to an embodiment of the present general inventive concept.

FIG. 2 is a flow diagram that schematically illustrates a method 100 of placing a stimulation element at a target stimulation site, according to an embodiment of the present general inventive concept. In some embodiments, method 100 is performed using substantially the same the systems, components, modules, functions, etc. as described in association with FIGS. 1 and 3-11. In other embodiments, method 100 is performed using other systems, components, modules, and/or functions available to those skilled in the art.

As illustrated by FIG. 2, method 100 includes advancing a stimulation element within a body, via an image-based navigation interface, to a target stimulation site, as at 102. In one embodiment, the stimulation element is advanced percutaneously while in other embodiments, the stimulation element is guided transvenously or through other access techniques. Each potential stimulation site is tested via observing neuromuscular responses produced from a stimulation signal (transmitted by the stimulation element), as at 104. In particular, a neuromuscular muscle response is determined separately for each potential target nerve stimulation site. In a superimposed combination with images of the location of the stimulation element among relevant anatomical structures (soft and hard tissues), the produced neuromuscular responses are displayed as a graphic identification of which muscle or multiple muscles were activated from a respective stimulation site, as at 106. In some embodiments, these muscle responses are recorded for later comparison to subsequent muscle responses. Further details for performing aspects of method 100 are described below.

FIG. 3 is a block diagram of a system 200 for providing image-based navigation of a stimulation element within a body while substantially simultaneously graphically identifying a target stimulation site (via the image-based navigation interface) via neuromuscular response evaluation, according to an embodiment of the present general inventive concept. As illustrated by FIG. 3, system 200 includes image-based navigation module 210, interface 212, and neuromuscular response evaluator 214, memory 216, and controller 218. In some embodiments, image-based navigation module 210, interface 212, and neuromuscular response evaluator 214 comprise at least substantially the same features and attributes as image-based navigation module 50, interface 30, and neuromuscular response evaluator 52, as previously described in association with FIG. 1.

In one embodiment, the interface 212 comprises a graphical user interface 280 configured to display, and enable operation of, the various parameters, components, functions, and modules of system 200. Accordingly, via interface 212, system 200 as illustrated in FIG. 3 represents the display of the respective parameters, components, functions, monitors, managers, and/or modules as well as representing the ability to activate or operate those respective parameters, components, functions, monitors, managers, and/or modules.

As illustrated by FIG. 3, image-based navigation module 210 includes image module 230, records function 64, anatomy map function 66, and fiducials function 256. The image module 230 obtains and provides to interface 212 one or more of a MRI image 240, a CT image 242, a fluoroscopy image 244, and/or an endoscopic image 245 of a pertinent region of a patient. In some embodiments, aspects of different types of images are synthesized or combined to yield a single hybrid image for display at interface 212. In one aspect, anatomical structures (such as, but not limited to, nerves and muscles) are located manually, and highlighted to the user at interface 212. For example, an operator can review available images of a patient body region and then select or indicate a particular structure of interest. In one non-limiting example, an operator selects a mandible within several different images or different image types so that the images can be integrated in a manner that still visually displays the anatomical structure of interest, i.e., the mandible. In another non-limiting example, an operator selects a nerve of interest from the soft tissues rendered by an MRI or selects the tongue or other upper airway muscles of interest and associates those with placed sensor/monitors. Records function 64 and anatomy function 66 comprise substantially the same features and attributes as previously described in association with FIG. 1.

Fiducials function 256 provides for visually tracking one or more fiducial markers that are visibly distinct from tissues on a displayed image to provide references points that are independent of the tissues and anatomical structures of interest. In some embodiments, locations for placing fiducial markers include one or more of an anterior point of the mandible bone, the hyoid bone, the skull, and/or cervical vertebrae. Of course, other or additional anatomical structures can be used as a fiducial reference point by placing a marker there. These fiducial markers have shapes and/or sizes selected to provide an objective orientation within and relative to the anatomical structures of the displayed image (e.g., displayed image 40 in FIG. 1) of interface 212. In one embodiment, during an imaging session to obtain images of relevant portions of patient anatomy, a radiopaque marker is placed at a desired implant site. Upon later use of fluoroscopy during placement of an implantable stimulation electrode, the radiopaque marker is easily identifiable and used as a general location marker to facilitate placement of the electrode.

Interface 212 of system 200 includes graphical user interface 280 (described above). In some embodiments, interface 212 includes target nerve identifier 282, target muscle identifier 284, actual nerve identifier 286, and actual muscle identifier 288, path marker function 290, target spot marker function 292, audio identifier module 300, and/or visual identifier module 320.

The actual nerve identifier 286 provides real-time visual identification of activated nerve(s) while the actual muscle identifier 288 provides real-time visual identification of activated muscle(s). Meanwhile, the target nerve identifier 282 and the target muscle identifier 284 provide time-independent display of a nerve intended to be stimulated and its innervated muscles that are intended to be activated. With these functions 282, 284 an operator designates on displayed image (e.g. displayed image 40 in FIG. 1) the respective nerve and muscle that are targeted. This designation is made via touching the respective portions of displayed image 40 (when interface 30, 212 includes a touch screen) or otherwise selecting the desired nerve and muscle via user controls 34 (such as a cursor navigation/selection or keypad entry).

In some embodiments, activation of path marker function 290 causes interface 212 to display a path through which the stimulation element 90 is expected to travel percutaneously (or otherwise internally in the body) as mapped out by an operator on a displayed image (e.g. displayed image 40 in FIG. 1) based on a probable target nerve stimulation site or a confirmed target nerve stimulation site. In some embodiments, target spot marker function 292 is provided to allow selective designation on a displayed image (e.g. displayed image 40 in FIG. 1) of a general or specific intended target site for placement of an implantable electrode. The accuracy of the target spot is confirmed or denied via the corroboration of neuromuscular response evaluation, and the target spot marker can be adjusted accordingly until an accurate target spot is located. Moreover, via target spot marker function 292, travel along the path is confirmed or evaluated by applying stimulation and observing which muscles are activated.

In some embodiments, the audio identifier module 300 comprises a hit function 302, a miss function 304, and/or an intensity function 306. In general terms, the audio identifier module 300 is configured to provide auditory identification of whether the intended target nerve is stimulated or not. In particular, feedback from which innervated muscle or muscles have been activated (via neuromuscular response evaluator 214) is communicated via an auditory signal, auditory words, or other easily recognizable auditory information. In some embodiments, the auditory alert occurs simultaneous with the period of activation of the muscle being stimulated. This auditory information communicates to the user whether the target nerve was activated or not. In some embodiments, this information is communicated as an audible alert by a spoken word, such as "hit", for activation of the target nerve (via hit function 302) and as a spoken word, such as "miss", for activation of a nerve other than the target nerve (via miss function 304).

The intensity function 306 of audio identifier module 300 provides an audio-based indication of an intensity of the muscle activation produced via nerve stimulation. In one aspect, this audio report is used to evaluate the intensity of the muscle response based on a given target nerve stimulation site This audio-intensity information communicates to the user a relative degree of stimulation of the target nerve, and relative effectiveness of a particular stimulation site on the nerve given a nominal set of stimulation parameters. In one example, a relatively low volume audio sound indicates a relatively low-to-moderate muscle activation to the operator while a relatively higher volume audio sound indicates a relatively high or robust degree of muscle activation. In addition, it will be understood that, depending upon the stimulation parameters, the relative effectiveness of a particular stimulation site might vary. Accordingly, in some embodiments, at each particular potential stimulation site along a nerve, the stimulation parameters are varied in an organized manner to fully evaluate the effectiveness of that potential stimulation site in activating an innervated muscle. The intensity of muscle activation for each different combination of stimulation parameters and/or stimulation site is reported to the operator via audio cues by audio identifier module 300.

To maximize the available information for decision making during percutaneous delivery of an implantable electrode or during initial determination of a stimulation site, in some embodiments the audio identifier module 300 is used in concert with the visual identifier module 320. However, it is understood that in other embodiments, just one of these respective identifier modules 300, 320 can be used. In still other embodiments, the audio identifier module 300 and the visual identifier module 320 are used simultaneously, but independent from each other.

With further reference to FIG. 3, in some embodiments, the visual identifier module 320 comprises a color function 322, a shading function 324, a numerical intensity function 326, a directional function 328, and/or a traced path function 330. In general terms, the visual identifier module 320 is configured to provide visual identification in interface 212 (such as interface 30 of FIG. 1) of whether the intended target nerve is stimulated or not. In particular, feedback from which innervated muscle or muscles have been activated (via neuromuscular response evaluator 214) is communicated via visual signals, visual words or symbols, or other easily recognizable visual information. This visual information communicates to the user whether the target nerve was activated or not. While this visual information can include graphical display of a signal normally associated with electromyography, in some embodiments, the displayed visual information omits ordinary waveform signals in favor of words, symbols, and other more readily identifiable information about the status of a particular muscle. In other words, visual identifier module 320 converts or evaluates the quantitative data of the EMG response and/or CMAP response into a qualitative form that quickly communicates, in a visually intuitive manner, to the operator which muscle has been activated and/or the intensity of the muscle response.

In one example, as noted above in association with FIG. 1, the visual identifier module 320 provides a graphical representation by which an activated muscle becomes highlighted on an image in a navigation interface such that the user can immediately recognize which muscle has been activated.

The color function 322 of visual identifier module 320 provides a color-based indication of which muscle is activated via nerve stimulation and/or a degree of muscle activation produced via nerve stimulation. This visual-intensity information communicates to the user a relative degree of stimulation of the target nerve, and relative effectiveness of a particular stimulation site on the nerve given a nominal set of stimulation parameters. In some embodiments, one color identifies a target nerve to be stimulated or a target muscle to be activated while a second color identifies which nerve is stimulated and/or which muscle is activated via a stimulation signal. In one embodiment, when the stimulated nerve matches the target nerve, a third color overlays the graphical representation of that target nerve to indicate that the target nerve was successfully located and was stimulated. Similarly, when the activated muscle matches the target muscle, the third color overlays the graphical representation of that target muscle to indicate that the target muscle was successfully located and was stimulated. It will be understood that the same color may be used for both nerves and muscles, or in other embodiments, that one set of colors is used to exclusively represent nerves and another different set of colors is used to exclusively represent muscles. Of course, it will be understood that other designations of colors can be used to communicate on a displayed image (e.g. displayed image 40 in FIG. 1) which muscles are actually activated via stimulation, which muscles are intended to be activated, and/or the degree of activation.

The shading function 324 of visual identifier module 320 provides a visual-based indication of which muscle is activated via nerve stimulation and/or a degree of muscle activation produced via nerve stimulation. A type of shading or a relative darkness of shading communicates to the user a relative degree of stimulation of the target nerve, and relative effectiveness of a particular stimulation site on the nerve (given a nominal set of stimulation parameters). In some embodiments, one type of shading is used to identify muscles and another type of shading is used to identify nerves.

In cooperation with the color function 322 and/or the shading function 324, the numerical intensity function 326 of visual identifier module 300 provides a visual-based numerical indication of an intensity of the muscle activation produced via nerve stimulation. This visual-intensity information communicates to the user a relative degree of stimulation of the target nerve, and relative effectiveness of a particular stimulation site on the nerve given a nominal set of stimulation parameters.

It will be understood that, depending upon the stimulation parameters, the relative effectiveness of a particular stimulation site might vary. Accordingly, in some embodiments, at each particular potential stimulation site along a nerve, the stimulation parameters are varied in an organized manner to fully evaluate the effectiveness of that potential stimulation site in activating an innervated muscle.

In one embodiment, the directional function 328 enables visual indication of directional movement of a stimulation element 90. However, in some embodiments, the directional function 328 provides a suggested direction in which to move the stimulation element. In this latter arrangement, the path analyzer 374 of neuromuscular response evaluator 214 evaluates the positive or negative outcome of the most recent stimulation sites (and the parameters of stimulation at those sites) and based on any recognized trends or patterns (from prior stimulation trials), then communicates a suggested direction of movement of the stimulation element. In one embodiment, the suggested direction is displayed graphically as a directional arrow on the displayed image (e.g. display image 40 in FIG. 1).

The traced path function 330 enables visual indication of a path of different previously tested stimulation sites and/or display of a path through which a stimulation element 90 is maneuvered through a body portion on the way to or from a stimulation site (or other target location).

With further reference to FIG. 3, in some embodiments, interface 212 includes a probe module 340 configured to track (based on a location of relevant EMG sensor probes and/or piezoelectric accelerometers) a target muscle, non-target nerves, and non-target muscles. In one embodiment, a target muscle parameter 346 of probe module 340 tracks, via a plurality of sensor probes configured to be removably coupled relative to a corresponding plurality of potentially activatable muscles, each potentially activatable muscle that is innervated by one of the potential target nerve stimulation sites. A non-target nerve parameter 344 of probe module 340 tracks, via a plurality of sensor probes configured to be removably coupled relative to a corresponding plurality of potentially activatable muscles, each potentially activatable muscle that is physically adjacent one of the potential target nerve stimulation sites and that is not targeted to be activated. Finally, a non-target muscle parameter 342 of probe module 340 configured to track, via a plurality of sensor probes configured to be removably coupled relative to a corresponding plurality of non-target muscles, each non-target muscle that is physically adjacent one of the target muscles.

In general terms, the neuromuscular response evaluator 214 of system 200 enables stimulation of nerves and muscles to identify a nerve stimulation site. In one embodiment, the neuromuscular response evaluator 214 includes a stimulation parameters module 350, a response module 352, and a stimulation element module 354.

In general terms, the stimulation parameters module 350 provides for selection of the various parameters of a nerve stimulation signal. In one embodiment, the stimulation parameters module 350 includes a pulse width parameter 360, frequency parameter 362, an amplitude parameter 364, a polarity parameter 366, and a duration parameter 368. Each of these parameters can be varied, as known by those skilled in the art, to achieve a desired stimulation signal on a nerve. The value of each of these parameters may vary from one stimulation site to another. It will also be understood, that in some embodiments, that a ground connection to the patient's body and a positive electrode will be used to enable, applying stimulation via a unipolar probe and identifying muscular responses.

The response module 352 provides for a mechanism to sense, record, and quantify neuromuscular responses of an activated muscle. In one embodiment, the feedback is sensed, recorded, and quantified via electromyography (EMG) via EMG function 380 while in some embodiments, the feedback is sensed, recorded, and quantified via compound muscle action potentials (CMAP) via CMAP function 382.

The stimulation path analyzer module 374 of response module 352 (of neuromuscular response evaluator 214) provides for differentiation between sources of stimulation of a sensed muscle response. In particular, a sensed muscle response can be caused by electrical stimulation of a nerve that innervates the muscle or by direct electrical stimulation of the muscle. Accordingly, the stimulation path analyzer module 374 is configured to sort data from the electromyography function 370 according to the stimulation parameters and navigation data (from image-based navigation module 210) to make this differentiation between nerve stimulation and direct muscle stimulation. Upon trying various potential stimulation sites, the path analyzer module 374 provides a graphical summary of which locations cause nerve stimulation and which cause direct muscle stimulation. With this information, a target stimulation site is selected.

In particular, in cooperation with EMG function 370 and by observing data produced via the compound muscle action potential (CMAP) function 372, the analyzer module 374 automatically determines if there is a time delay between the electrical stimulation and the ensuing muscle activation. In particular, if direct electrical stimulation was performed on a target muscle, then no delay would be expected between that stimulation and the ensuing muscle activation. However, if electrical stimulation was performed on a target nerve, then a delay would be expected between that stimulation and the ensuing muscle activation. In one example, an approximately 100 microsecond delay would be expected for each 1 centimeter distance that the muscle is located away from the nerve. As described later in association with FIG. 6B, this muscle response time is tracked via a nerve-muscle index 294.

The ability to automatically differentiate between electrical nerve stimulation and direct muscle stimulation via path analyzer 374 greatly facilitates percutaneous determination of a location of a target stimulation site of a target nerve because, in that situation, the user typically does not have direct physical sight of the nerves and/or muscles at which the stimulation tool is directed. However, via the analyzer module 384, system 200 is able to determine which nerve or muscle is being stimulated, and which muscle is activated as a result. Upon attempting stimulation at several different locations percutaneously with the stimulation element, the user determines which anatomical structure (e.g. target nerve) at which an implantable electrode should be located and at which location or position along that nerve the electrode should be secured.

Moreover, once the target stimulation site is determined, the user can further utilize system 200 to determine a pathway through which the electrode can be delivered percutaneously to arrive in the desired position at the target stimulation site.

In some embodiments, the analyzer module 374 determines a strength-distance curve for activation of target muscle groups. In one aspect, the strength-distance curve includes a graphic representation of the relationship between an intensity of the electric stimulation site and a distance between the actual stimulation site and the target nerve. Accordingly, using this strength-distance curve, a distance is estimated between the location of the stimulation element and the activated nerve (or activated muscle). This distance information is used by the physician to determine how much further, and in which direction, to maneuver the stimulation element to arrive at the desired location or position relative to the target stimulation site. In some embodiments, this information is communicated via directional function 328 of interface 212. In addition, once a final placement of the stimulation element (e.g. cuff electrode) is determined, a strength-duration curve produced via analyzer module 374 (in association with CMAP function 372 and EMG function 370) facilitates a physician (or programming unit) in setting efficacious stimulation therapy settings to treat a physiologic condition, such as sleep-disordered breathing behaviors.

In some embodiments, system 200 includes a nerve-muscle index module 294 configured to correlate observed muscle response behavior with an associated nerve innervating the respective muscles. This index 294 can aid in placing sensor probes and/or in identifying a stimulation source upon observed muscle responses. In some embodiments, the interface stores in memory an array of nerve-muscles indices with a separate nerve-muscle index for each separate patient body portion. In addition, in some embodiments, a nerve-muscle index for a particular patient body portion is loaded into a memory of the system prior to performing a method of percutaneously advancing a stimulation element into and through that particular body portion. Further details regarding the nerve-muscle index 294 are described and illustrated later in association with FIG. 6B.

In some embodiments, response evaluator 352 also comprises an ultrasound detection function 375 which is configured to detect muscle motion according to Doppler principles. For example, via an ultrasound sensor node placed underneath the chin, ultrasound detection function 375 detects motion of the genioglossus muscle in response to stimulation at or near a target stimulation site. In another example, via an ultrasound sensor node placed at the jaw, ultrasound detection function 375 detects motion of the styloglossus muscle in response to stimulation at or near a target stimulation site. Information gained via the ultrasound detection function 375 is deployed in at least muscle motion parameter 476 in nerve-muscle index 294, as later described in association with FIG. 6B.

Stimulation element module 354 provides for applying electrical stimulation via a test tool 380 and/or an implantable electrode 382. In most instances, the test tool 380 is employed by the physician to first identify the target nerve(s) and target muscle(s) in cooperation with the other functions, modules of interface 212 and system 200. Thereafter, using the image-based navigation interface provided according to general principles of the present general inventive concept, the electrode 382 is delivered percutaneously to the target stimulation site with or without the assistance of test tool 380. It will be understood that in such a procedure, the patient is under anesthesia and without using muscle relaxants.

In either case, in some embodiments, the stimulation element module 354 includes a handle control portion 384 for guiding test tool 380 or electrode 382. The handle control portion 384 includes an on/off function 386, increase function (+) 388, decrease function (−) 390, pause function 392, and mode function 394. The respective increase and decrease functions 388,390 provide for a corresponding increase or decrease in the stimulation parameters (such as amplitude, pulse width, etc.) while the pause function 392 allows temporary suspension of the stimulation signal. The mode function 394 allows selecting various modes of stimulation, such as continuous, intermittent, or discrete (just when an input button is pressed). In some embodiments, the mode function 394 includes an automatic ramping function to determine the parameters 360-368 of module 350 of stimulation (such as amplitude, pulse width, frequency, polarity, duration) needed to recruit the targeted nerve and innervated muscles. Accordingly, this automatic ramping function provides information regarding the efficaciousness of the current stimulation location and the observed muscle responses. For example, a muscle response to a direct electrical stimulation of the muscle is generally less than a muscle response to electrical stimulation of the nerve that innervates the particular muscle. In another example, lower stimulation amplitudes required to produce a muscle response generally indicate that a stimulation element is close to the target nerve, whereas higher stimulation amplitudes required to produce a muscle response generally indicate that a stimulation element is further from the target nerve than desired.

Controller 218 comprises one or more processing units and associated memories 216 configured to generate control signals directing the operation of system 200 and its components. For purposes of this application, the term "processing unit" shall mean a presently developed or future developed processing unit that executes sequences of instructions contained in a memory, such as memory 216 or other memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 218 may be embodied as part of one or more application-specific integrated circuits (ASICs). Unless otherwise specifically noted, the controller is not limited to any specific combination of hardware circuitry and software, nor limited to any particular source for the instructions executed by the processing unit.

Figure 4:
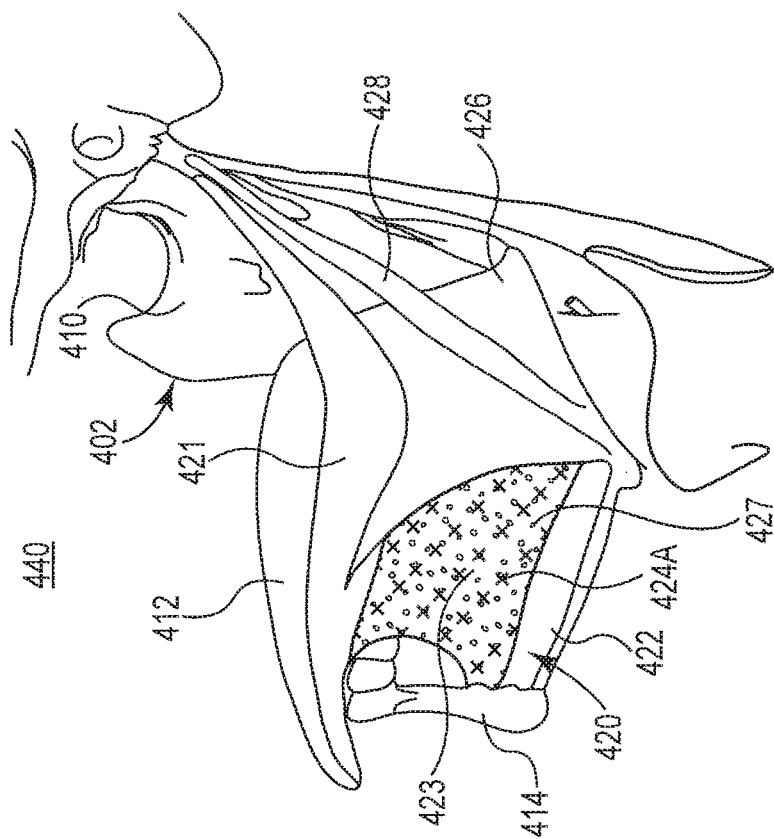
FIGS. 4-5 are a side plan view schematically illustrating an interface of a method and system for graphical differentiation between a target muscle and an activated muscle, according to an embodiment of the present general inventive concept.

FIG. 4 is side view schematically illustrating an image-based user interface that visually identifies muscle activation, according to an embodiment of the present general inventive concept, for use in percutaneous navigation and/or percutaneous placement of a stimulation element. As illustrated by FIG. 4, image 400 graphically depicts a body portion 402, such as a head-neck region of a patient. The body portion 402 includes bony structures 410 that support a group 420 of muscles and tissues. In the example shown, bony structures 410 include a lower jaw portion 414 that supports a tongue 412 and its underlying muscles, including (but not limited to) a stylo-glossus muscle 421, a genio-hyoideus muscle 422, a genio-glossus muscle 423, a hyo-glossus muscle 426, and a stylo-hyoideus muscle 428.

In one embodiment, the genioglossus muscle 423 as shown in FIG. 4 is a target muscle that is desired to be activated. In particular, activation of this genioglossus muscle 423 contributes to protrusion of tongue 412 forward, thereby increasing airway patency near the base of the tongue. In some instances, this protrusion produced via activating the genioglossus muscle 423 is used to treat sleep-disordered breathing behaviors, such as obstructive sleep apnea. In one embodiment, the designation of this muscle as a target muscle is graphically depicted via a pattern 424A.

As further shown in FIG. 4, instead of target muscle 423 being activated, the hyo-glossus muscle 426 is activated, as graphically depicted via a pattern 427.

By displaying this juxtaposition of pattern 424A for target muscle 423 and pattern 427 for the actually activated muscle 426, the interface (30,212) provides an immediately recognizable differentiation between the activated muscle and the target muscle, and thereby indicates that the stimulation site did not result in activation of the target muscle and indicates which muscle (e.g. muscle 426) was activated. This differentiation informs the user that a different stimulation site should be selected.

In some embodiments, upon such differentiation, system 200 (FIG. 3) suggests graphically (e.g. via highlighting) which nerve to stimulate instead of the previously stimulated nerve or directly stimulated muscle. Moreover, in some embodiments, this suggestion is communicated via directional arrows, as provided via directional function 328 of visual identifier module 320 (FIG. 3).

Figure 5:
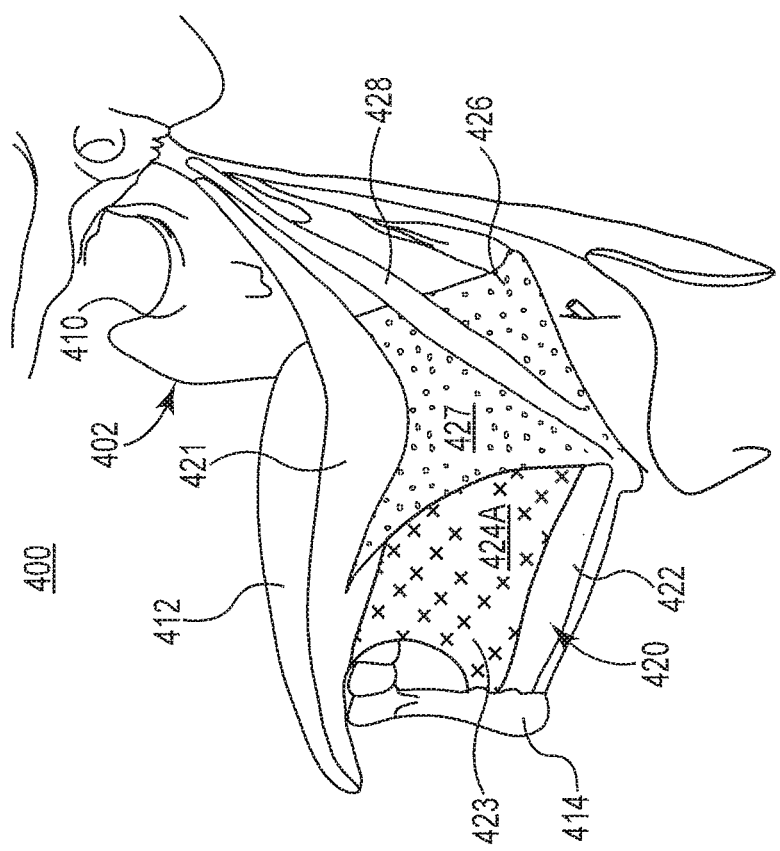

FIG. 5 schematically illustrates substantially the same features and attributes as FIG. 4, except for illustrating that the activated muscle (represented by dotted pattern 427) substantially coincides with the target muscle (represented by cross-shaped pattern 424A). Alternatively, an entirely different graphical pattern can identify the convergence of the activated muscle and the target muscle.

This arrangement provides easier and more effective indication to a user of when a target stimulation site has been located by visually identifying the corresponding innervated muscle upon its activation. Moreover, interface 212 graphically displays via highlighting which nerve was stimulated and, via a graphical marker or highlighting, the precise location along that nerve at which the stimulation was applied. Moreover, even after the stimulation element is selectively deactivated, interface 212 allows the user to mark (or automatically marks) the stimulation site, such as via target spot marker function 292.

In some embodiments, the graphical patterns 424A, 427 are replaced with shading via shading function 324 and/or replaced with color via color function 322 of visual identifier module 320 (FIG. 3).

Figure 6A:
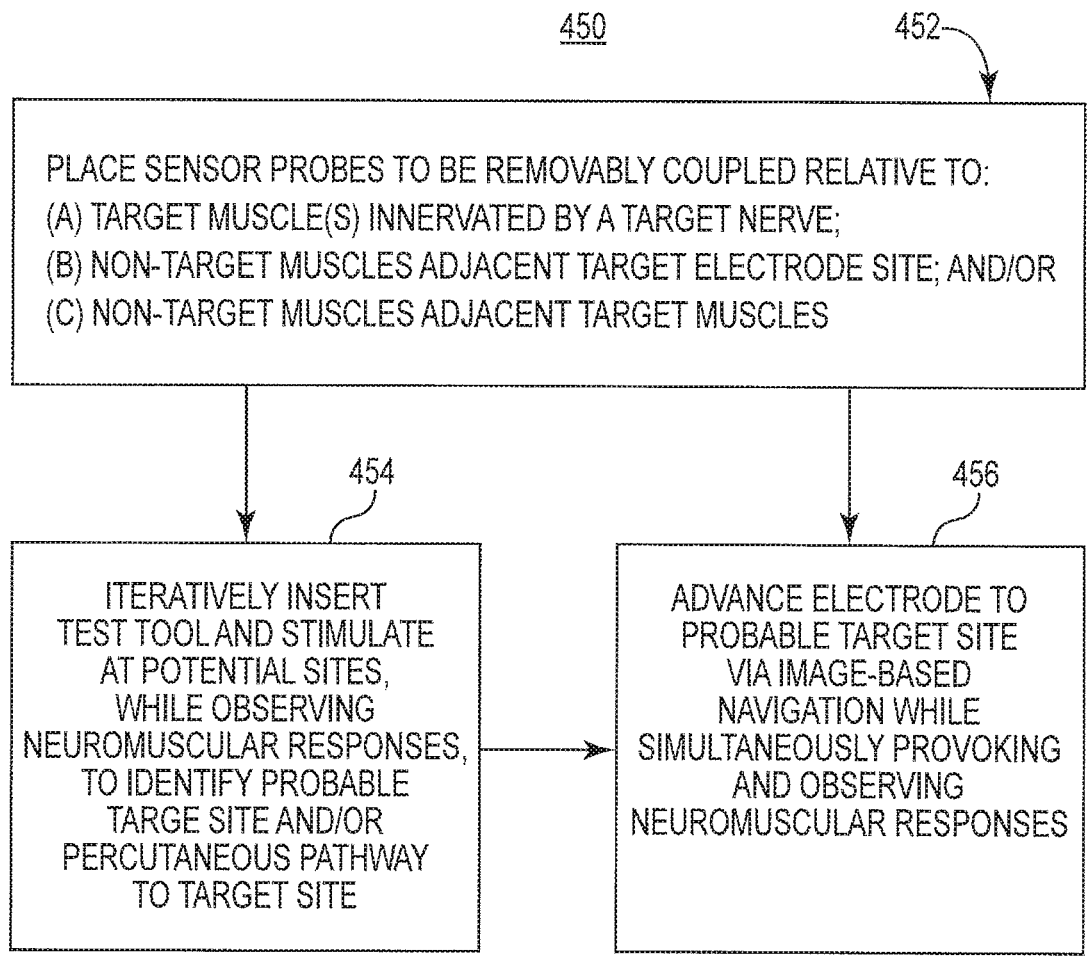
FIG. 6A is a flow diagram of a method of identifying a stimulation site via an array of sensor probes, according to an embodiment of the present general inventive concept.

FIG. 6A is a flow diagram schematically illustrating a method 450 of identifying a target stimulation site, according to an embodiment of the present general inventive concept. In one embodiment, method 450 is performed using the systems, components, and modules as previously described in association with FIGS. 1-5. In some embodiments, other systems and components are used to perform method 450.

As shown in FIG. 6A, method 450 includes placing sensor probes onto various portions of a patient body portion in order to removably couple each sensor probe relative to a respective one of a plurality of muscles of the patient body portion. These muscles can include a target muscle innervated by a target nerve, non-target muscle(s) adjacent a target electrode site along the target nerve, and/or non-target muscles adjacent the target muscle(s), as shown at 452. Placement of sensor probes on these non-target muscles allows sensing the activation of the non-target muscles adjacent either the target nerve site or the target muscle, which is in turn, indicative of sub-optimal electrode positioning relative to a target nerve site. When graphically identified in an image-based navigation interface (or via direct observation of a functional result, such as tongue protrusion) sensing activation of the non-target muscles provides feedback to re-position the stimulation element toward the target nerve site.

Accordingly, sensor probes are placed at locations of muscles near the nerve to be stimulated and locations of muscles (or muscle groups) likely to result in muscle activation, whether or not those muscles are the target muscles. With the sensor probes arranged in this manner, upon implementing the nerve stimulation a displayed image (e.g. displayed image 40 in FIG. 1) in interface 30, 212 will highlight which muscles are activated for each trial stimulation, as noted below.

In one embodiment, method 450 proceeds from the sensor probe placement at 452 to use a test tool (not an implantable electrode) for iterative insertion to stimulate potential sites while observing neuromuscular responses, as highlighted on displayed image (e.g. displayed image 40 of FIG. 1) of interface 30, 212 to identify a probable target site and/or a probable percutaneous pathway to the target site. Thereafter, at 454, method 450 proceeds to advancing an implantable nerve stimulation electrode to a probable target site via image-based navigation while simultaneously provoking and observing neuromuscular responses. However, in performing method 450, one need not use the test tool (at 454) prior to advancing the implantable electrode within the pertinent body region (at 456).

In one embodiment, method 450 is performed in association with nerve-muscle index 294 (FIGS. 3 and 6B), among other resources of system 200. In one aspect, the nerve-muscle index 294 provides a basis to build a graphical user interface (e.g. user interface 30, 40 of FIG. 1) by adding the monitored tissues to the skeletal outline. The nerve-muscle index 294 also provides an additional portion of interface 30 (as described later in association with FIG. 12) or alternate view (such as FIG. 6B) that supplements the visual representation of the current location of the stimulation electrode and sensor probes (in interface 30) by supplying a checklist of which muscle groups are activated or inactivated.

Figure 6B:
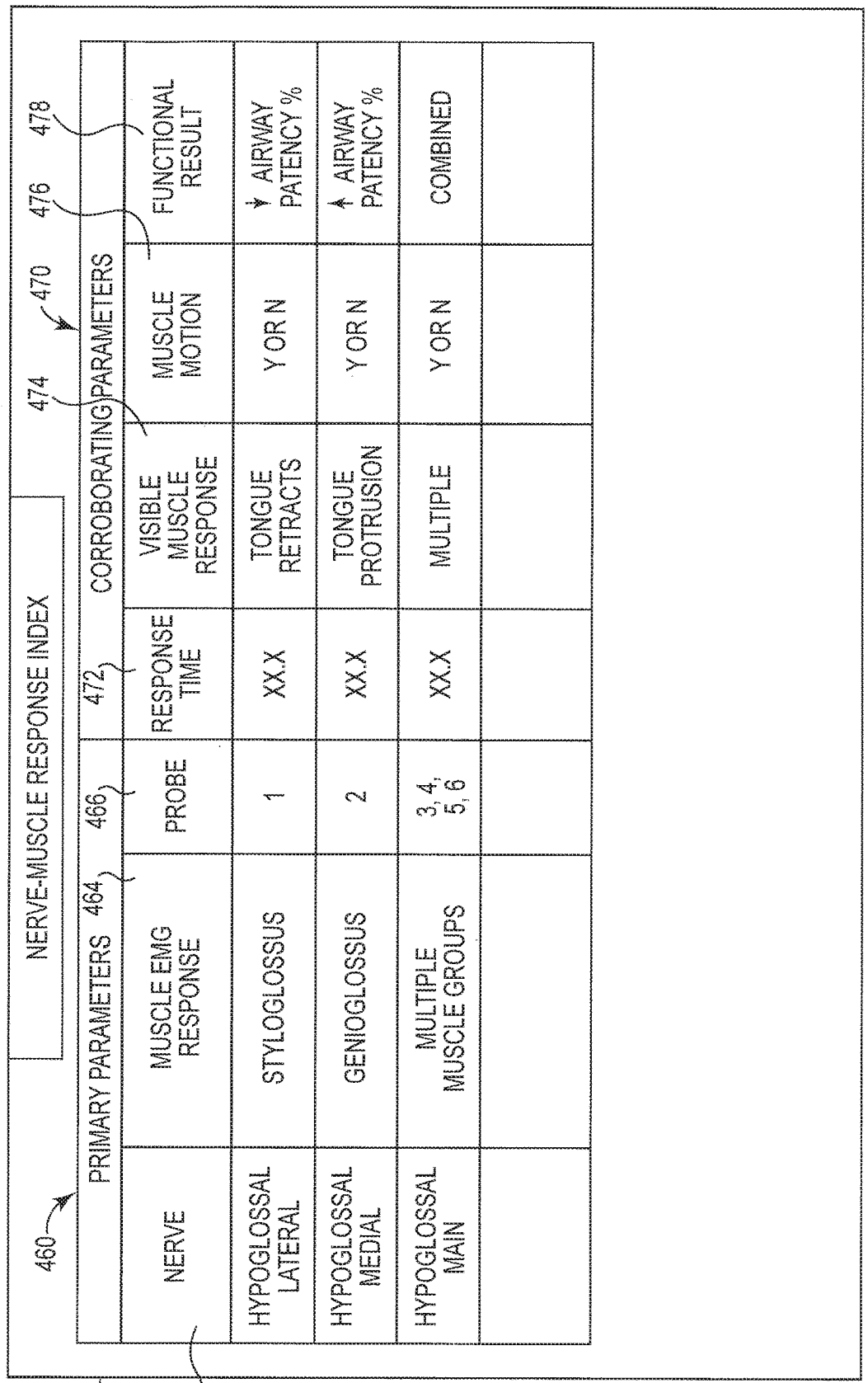
FIG. 6B is a block diagram of a nerve-muscle response index, according to an embodiment of the present general inventive concept.

As illustrated by FIG. 6B, in some embodiments, the nerve-muscle index 294 comprises an array 460 of primary parameters and an array 470 of corroborating parameters. The array 460 of primary parameters includes a nerve parameter 462, a muscle response parameter 464, and a probe parameter 466. The nerve parameter 462 maintains a list of nerves of the patient body portion while the muscle response parameter 464 maintains a list of muscles that respond to and that are innervated by a respective one of the listed nerves. In addition, the muscle response parameter 464 tracks an amplitude of muscle response for a particular muscle upon nerve stimulation. By comparing different stimulation sites and an amplitude of the muscle response (such as through electromyography), one can map the location of a target nerve. The probe parameter 466 maintains a listing of the various sensor probes that are removably coupled to the respective muscles with each sensor probe matched to a particular muscle. Accordingly, via index 294, each listed muscle is correlated to one of the respective sensor probes and relative to a respective one of the potential target nerves that innervate the respective listed muscle.

With further reference to FIG. 6B, in one example, via index 294, a lateral branch of the hypoglossal nerve is correlated with a styloglossus muscle and sensor probe number 1. Accordingly, when a response is observed for sensor probe 1, the system automatically determines that the response is for the styloglossus muscle and an accompanying graphical identification is made on the user interface to visually highlight the activation of that muscle. In another example, via index 294, a medial branch of the hypoglossal nerve is correlated with a genioglossus muscle and sensor probe number 2. Accordingly, when a response is observed for sensor probe 2, the system automatically determines that the response is for the genioglossus muscle and an accompanying graphical identification is made on the user interface to visually highlight the activation of that muscle. As further illustrated in index 294, additional nerves or nerve branches are listed, such as the main trunk of the hypoglossal nerve, which activates several muscle groups, and which is associated with multiple sensor probes distributed across the multiple muscle groups. Accordingly, in cooperation with interface 40 (FIG. 1), nerve-muscle index 294 enables an operator to differentiate which nerve branch is being stimulated, among multiple potential target nerve branches, and therefore, responsible for activation of a particular muscle group or muscle groups.

The array 470 of corroborating parameters is used to confirm the identity of the muscle that was activated and/or whether the muscle activation resulted from nerve stimulation or direct electrical stimulation of the muscle. In some embodiments, the array 470 of corroborating parameters includes a muscle response time parameter 472, a visible muscle response parameter 474, a twitch response parameter 476, and a functional result parameter 478.

In some embodiments, the response module 352 of interface 212 (FIG. 3) is configured to confirm that the target nerve identified via the nerve-muscle response index caused the activation of the respective listed muscle. In one embodiment, this confirmation is executed via a response time function and tracked as a response time parameter 472 in index 294. The response time parameter indicates the amount of time between a stimulation of a nerve and when the response is observed at the muscle (innervated by that stimulated nerve). This information is used to determine whether the activation of muscle was caused by electrical stimulation of the nerve or by direct electrical stimulation of the muscle, as the direct electrical stimulation of the muscle would result in a response time of near zero.

Moreover, the response time of a particular muscle depends on the location of stimulation along the nerve and its respective branches. Conceptually speaking, one can divide the nerve into segments with each segment innervating a particular set of muscles. By using the measured reaction time and observing which muscle group is activated, one can determine the location of stimulation, and therefore which nerve or nerve branch was stimulated. In some embodiments, in accordance with general principles of the present general inventive concept, this process can be performed in whole, or in part, according to the methods and systems described and illustrated in association with Testerman U.S. Pat. No. 5,591,216.

In some embodiments, a visible muscle response parameter 474 of index 294 is configured to indicate a visible muscle response that a user could observe, such as whether the tongue retracts which corresponds to activation of tongue protrusor muscles, such as a styloglossus muscle listed in the muscle response parameter 464. If the observed behavior upon application of a stimulation signal matches the expected response for a target nerve, then one gains assurance that the target stimulation site has been identified. On the other hand, if the observed behavior upon application of a stimulation signal does not match the expected response for a target nerve, then one learns that the target stimulation site has not been identified. In the latter case, upon repositioning a stimulation element, a subsequent stimulation signal is applied to activate a muscle and the response is observed to evaluate whether the target site has been identified.

In some embodiments, the muscle motion parameter 476 of index 294 is configured to track whether motion of the muscle can be detected, whether or not that also results in a highly visible response (such retraction or protrusion of the tongue). In one embodiment, the detectable muscle motion parameter 476 tracks muscle responses via ultrasound sensor nodes that detect muscle motion via Doppler principles. For example, in response to a stimulation of a nerve, motion of the genioglossus muscle is detectable via an ultrasound sensor node placed underneath the chin while motion of the styloglossus muscle is detectable via an ultrasound sensor node placed through the jaw. In cooperation with interface 40 and ultrasound detection function 375 of response evaluator 352 of system 200 (FIG. 3), a corresponding anatomical feature (e.g. nerves and muscles) is highlighted in image 30 (FIG. 1), in index 294 (FIG. 6B), or combined interface 700 (FIG. 12) upon ultrasound detection of motion for a particular muscle or nerve.

In another embodiment, the detectable muscle motion parameter 476 tracks whether a twitch response of a muscle is observed, which can further corroborate which nerve was stimulated by which muscle responds via the twitch.

Figure 13:
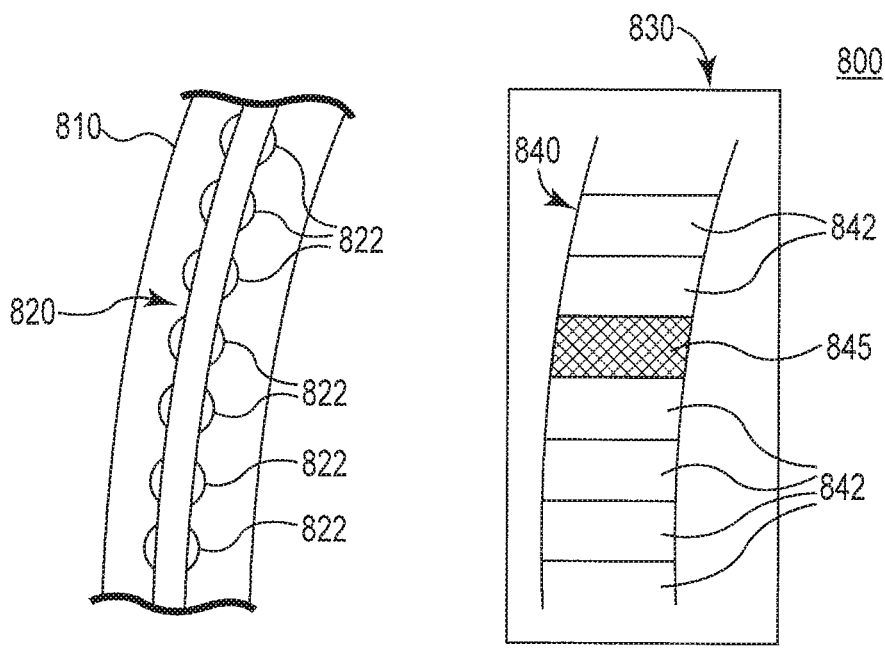
FIG. 13 is a schematic illustration of a multi-balloon probe and display of pressure sensed via the probe, according to an embodiment of the present general inventive concept.

Likewise, the functional result parameter 478 of index 294 is configured to identify what functional result (e.g. an increased or a decreased percentage of airway patency) would be observed upon activation of a particular muscle, which in turn helps to determine if the target nerve or portion of the target nerve was stimulated. For example, observation and/or measurement of the cross-sectional area of upper airway patency indicates whether the desired muscle response is achieved in response to a test stimulation at a target nerve site. In another example, a functional result tracked via parameter 478 includes a relative amount and location of air pressure within the upper airway 810 as indicated via a multi-sensor catheter probe 820, as illustrated in FIG. 13. As shown in FIG. 13, the multi-sensor probe 820 extends within upper airway 810 and includes an array of linearly arranged pressure-sensitive sensors 822 programmed to separately indicate a measured pressure at each sensor 822. Upon an obstruction occurring in the airway 810, the air pressure adjacent one or more of the sensors 822 will be significantly impacted, and thereby indicate a location of the obstruction along the airway. In one embodiment, each separate sensor 822 comprises a mini-lumen exposed to the air within the upper airway and in communication with a pressure transducer so that the air pressure is measurable at each location of the respective sensors 822 along the length of probe 820, thereby indicating the air pressure at different locations within the airway. In some other embodiments, each sensor 822 comprises a balloon-like structure adapted to measure the air pressure at each location of the respective sensors 822.

FIG. 13 also illustrates an image 830 displayable in a user interface, such as interface 30 in FIG. 1 or in functional result display 710 of interface 700 in FIG. 12, as will be described further. Image 830 displays an image 840 of airway 830, with the airway 830 schematically or graphically divided into segments 842 with each segment 842 generally corresponding to a location of a sensor 822. Based on the sensed pressures, image 840 indicates a location of obstruction from a sleep-related breathing disorder (such as obstructive sleep apnea) via highlighter indicator 845. This information is also used to evaluate whether stimulation of a target stimulation site on a nerve, results in a muscle response that opens the airway 830 in the vicinity of likely obstruction, such as marked visually via identifier 845.

In one embodiment, information available from nerve-muscle response index 294 (such as the corroborating parameters of array 470) is graphically displayed at the user interface at the time that a muscle is stimulated to aid the user in identifying corroborating information, such as a twitch or functional result, by reminding the user what behavior is to be observed.

In some embodiments, in addition to the image 40 being displayed in interface 30 (FIG. 1), a nerve-muscle index (including at least some of the features of nerve-muscle index 294 of FIG. 6A) is displayed in interface 30 along with image 40 and/or alternately with image 40. The displayed index lists a plurality of muscle groups for which a response is expected upon application of the stimulation signal, such as the listings in index 294. In some embodiments, the displayed index includes, but is not limited to, one or more of: (1) a description of an expected muscular response resulting from application of the stimulation signal at the target site; (2) highlighting, upon activation via the stimulation signal, at least one of the respective muscle groups listed in the index; and (3) data surrounding the muscular response including at least one of a response time and a response amplitude. In addition to supplementing the information displayed via image 40 in user interface 30, the nerve-muscle index aids in displaying or identifying to the user, which muscle group has been activated in the event that the graphical display of the activated muscle in image 40 is difficult to see.

In some embodiments, the nerve-muscle index 294 also lists one or more muscle groups for which stimulation is neither desired nor expected. To the extent that these respective muscle groups do not become highlighted in the nerve-muscle index 294, the physician receives assurance that undesirable neuromuscular stimulation is avoided. However, in the event that such undesirable neuromuscular stimulation does occur and that particular muscle group was highlighted, the nerve-muscle index 294 provides one warning mechanism to alert the physician of undesirable stimulation.

In some embodiments, the nerve-muscle index 294 is storable in memory and suitable for printing to provide a record of the navigation process and/or implantation procedure of an implantable stimulation electrode.

Figure 12:
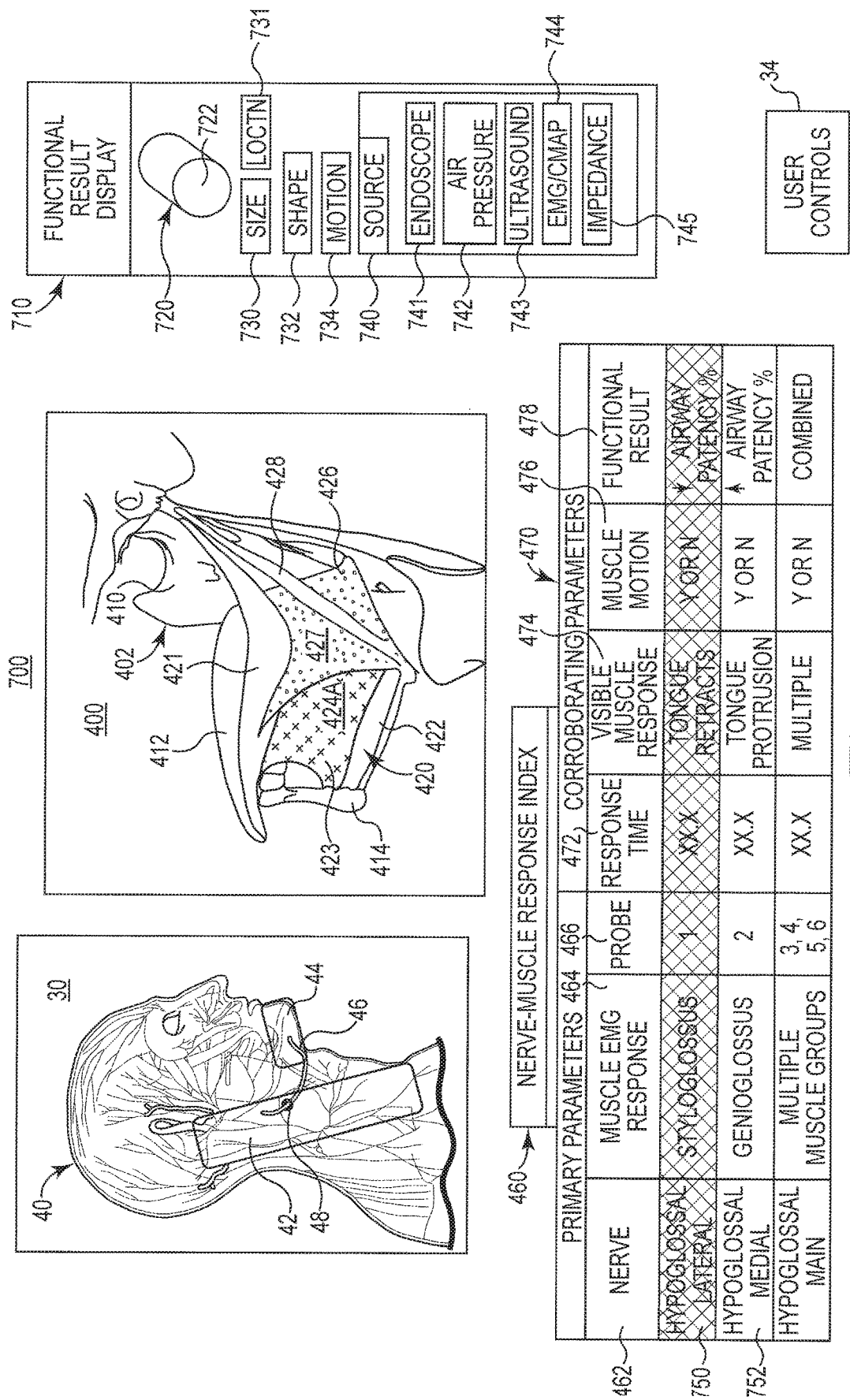
FIG. 12 is a schematic illustration of a system and user interface for navigating a path to implant a stimulation element and simultaneously evaluate, via graphic displays, in real-time whether the path or stimulation site is efficacious, according to an embodiment of the present general inventive concept.

In one embodiment, an interface 700 that includes a combination of image 40 and nerve-muscle index 294 is described and illustrated in association with FIG. 12. As shown in FIG. 12, interface 700 includes the interface 30 (FIG. 1), the interface 400 (FIG. 4), nerve-muscle index 460 (FIG. 6B), each having substantially the same features and attributes as previously described and illustrated in association with those respective Figures. In addition, in some embodiments, interface 700 further includes functional result display interface 710. As shown in FIG. 12, interface 710 includes an image 720 of an anatomical feature (e.g., a cross-sectional view 722 of the upper airway viewable via endoscopy) pertinent to observing a functional result of stimulating a target nerve. Interface 710 also includes a size parameter 730, a shape parameter 732, a location parameter 731, a motion parameter 734, and a source function 740. The size and shape parameters 730, 732 track a change in the size or shape of an anatomical feature. For example, an upper airway can exhibit a general reduction in its cross-sectional area while maintaining a generally circular cross-sectional shape or alternatively could exhibit a significant reduction in its cross-sectional area as the generally circular shape disappears as the airway generally collapses. The location parameter 731 tracks a general anatomical location and/or a specific location on an anatomical feature at which a functional result can be observed or measured. The motion parameter 734 indicates whether or not motion has occurred (e.g. does tongue protrude?) upon stimulation at a target site.

The source function 740 tracks a source by which an image (or other graphical display) of a functional result is obtained or produced. In some embodiments, source function 740 includes an endoscope parameter 741, an air pressure parameter 742, an ultrasound parameter 743, an EMG/CMAP parameter 744, and an impedance parameter 745. Each respective parameter 741-745 provides information consistent with the previously described sensing or detecting functions. For example, ultrasound parameter 743 provides information available via ultrasound detection function 375 (FIG. 3) while air pressure parameter 743 provides information available via multi-balloon catheter probe 820 (FIG. 13).

In general terms, interface 710 offers a highly integrated display to facilitate navigation of a stimulation element and/or related tools by graphically displaying anatomical features (e.g., bones, tissues, etc.) and the instruments in the field of navigation in real time as the instruments are moved along a navigation path. Moreover, at the same time, interface 710 displays, in real-time, a functional visualization of whether a given path or nerve stimulation test site produces a desired functional result of the intended or target muscle. This functional visualization is coordinated with images of the navigation field so that the navigational information and the functional result information is displayed in a single interface to aid the operator with real-time information that facilitates more accurate navigation and placement of a stimulation element or test tool. As further illustrated in FIG. 12, nerve-muscle index 460 provides additional text information in real-time to aid the operator in quickly corroborate the visual/graphic information displayed at interfaces 40, 400, or 710 in interface 700. For example, index 460 in FIG. 12 includes a highlighting function 750 in which a nerve or innervated muscle of interest (such as a nerve being stimulated) is highlighted in index 460 (represented by shading) and which corresponds to a highlighted nerve and/or innervated muscle in interface 40, 400, or 710. It will be understood that, in some embodiments, interface 700 is selectable controllable to display a subset of the interfaces 40, 400, 710 and index 460, at the discretion of the operator.

Figure 7:
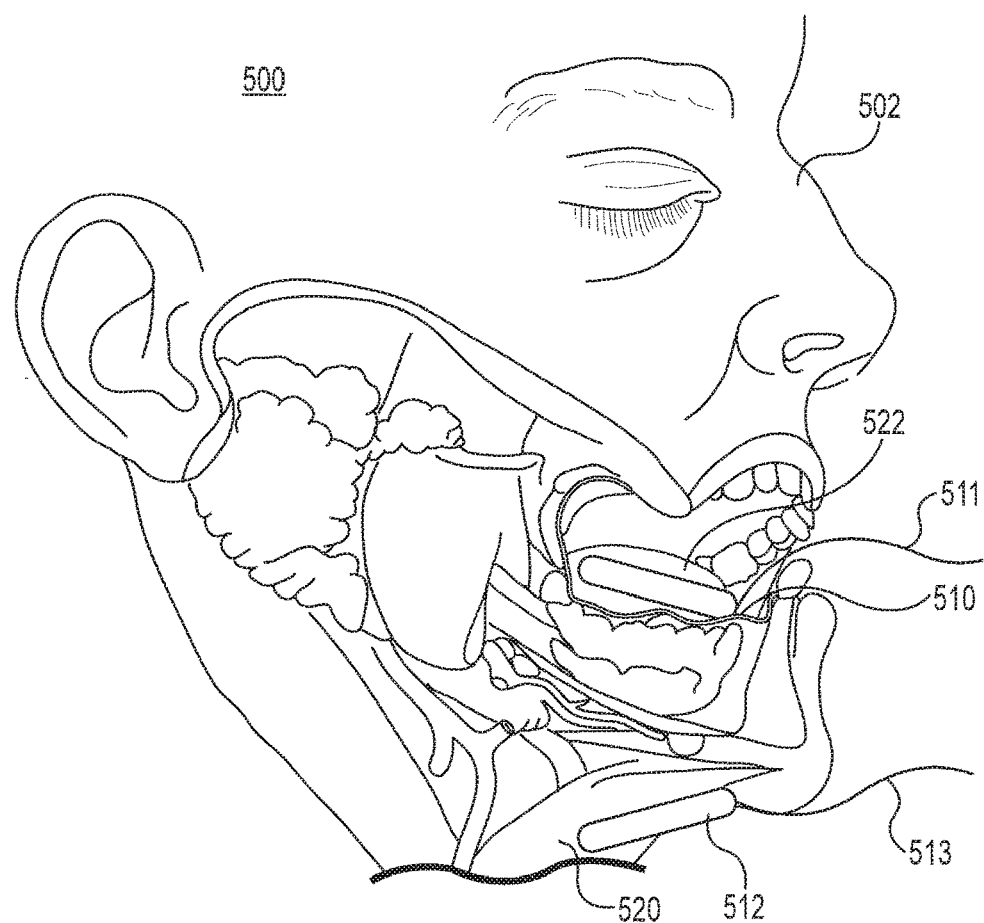
FIG. 7 is a side view schematically illustrating a method of sensing neuromuscular responses via sensor probes in a head region of a patient, according to an embodiment of the present general inventive concept.

FIG. 7 is a side view schematically illustrating an arrangement 500 of placed sensor probes (510, 512) for detecting impedance changes indicative of a functional response of a target muscle, according to an embodiment of the present general inventive concept. In particular, FIG. 7 illustrates a head region 502 of patient and in particular, an oral and neck region including tongue 522 and airway patency-related muscle 520. In one aspect, probe 510 is placed on tongue 522 while probe 512 is placed under the jaw adjacent airway patency-related muscles 520. With this arrangement, impedance is measurable with the two probes 510, 512 such that changes in impedance can be used to quantify movement of the tongue. In particular, increased impedances to the electrodes near the front of the tongue and the back of the airway would be indicative of a substantial forward movement of the tongue.

In general terms, correct placement of a probe can be confirmed by applying stimulation to one probe and then sensing the response from other probes or observation by a physician. While some probes may not be placed in ideal locations, it will be understood that whatever information is obtained from these probes is used to help determine or corroborate an intended navigation path and/or identification of a target stimulation site.

Figure 8:
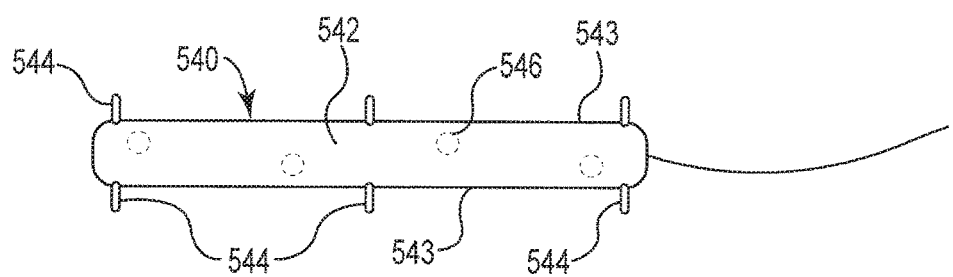
FIG. 8 is a top plan view of a sensor probe, according to an embodiment of the present general inventive concept.
Figure 9:
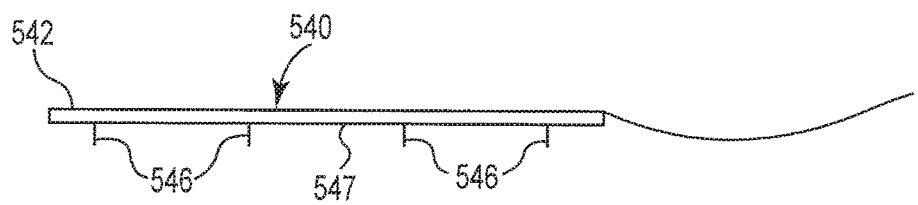
FIG. 9 is a side plan view of a sensor probe, according to an embodiment of the present general inventive concept.

FIGS. 8-9 further illustrate a sensor probe 540 (that can act as probe 510 and/or 512) according to an embodiment of the present general inventive concept. FIG. 8 is a top view of probe 540, which includes a generally elongate flexible body 542 made of (or coated with) a biocompatible material. In some embodiments, probe 540 includes a plurality of anchors 544 that extend from opposite side portions 543 of body 542 and are spaced apart from each other longitudinally along a length of body 542. Each anchor 544 includes a pressure sensitive adhesive on its underside to allow secure direct adhesion relative to a surface body portion. However, in other embodiments, it will be understood that any number of different types of fasteners can be used with, or in place of, anchors 544. In some embodiments, additional fastening is achieved via coating the underside 547 of body 542 with adhesive.

FIGS. 8-9 further illustrate that probe 540 includes an array of fine gauge needles 546 arranged in a spaced apart relationship along the length of body 542, and extend away from an underside 547 of body 542. In one embodiment, the needles 546 extend generally perpendicular to the underside 547 of body 542 although in other embodiments, needles 546 can extend at different angles relative to underside 547.

While FIG. 7 provides one schematic illustration of probe placement, it will be understood that can have more than two sensors and that sensors can be placed in other locations. For example, as described previously, in some embodiments, some sensor probes are placed at the target muscle groups (i.e. the intended muscle to be activated) to confirm that the desired muscle group is activated and to obtain data re stimulation, muscle response, etc. In addition, in some embodiments, sensor probes are placed at muscle groups near the target nerve to facilitate optimal electrode placement. In particular, an observed activation of a muscle near the target nerve site would indicate a likely sub-optimal electrode placement at the target nerve, and thereby trigger the physician to adjust the placement of the electrode.

Figure 10:
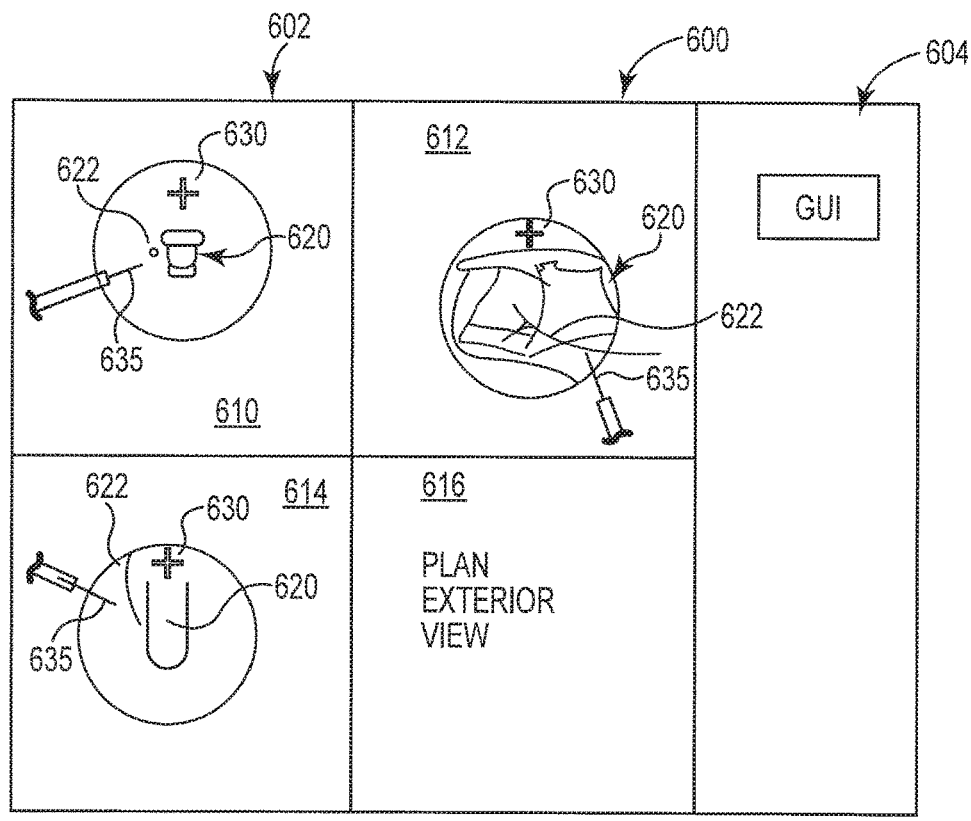
FIG. 10 schematically illustrates a system and user interface for navigating a pathway via images in relation to neuromuscular responses, according to an embodiment of the present general inventive concept.

FIG. 10 is a schematic illustration of an image-based visualization system 600 used in a method of identifying a target stimulation location, according to an embodiment of the present general inventive concept. As shown in FIG. 10, system 600 includes an image module 602 and graphical user interface 604. In one embodiment, system 600 corresponds to a StealthStation™ type imaging system available from Medtronic of Fridley, Minn. As shown in FIG. 10, image module 602 provides internal images of anatomical structures of a body region, with image module 602 including a front view 610, a side view 612, a top view 614, and a plan exterior view 616. The front view 610 and top view 614 illustrate a body region including a tongue portion 620 and a nerve 622. Marker 630 provides an independent reference point, such as a fiducial marker. The side view further illustrates the tongue portion 620 and nerve 622, although showing the various muscle groups (see also FIGS. 4-5) supporting tongue portion 620. Using the various views of the image module 602 to collectively provide a three-dimensional view, an operator can guide a stimulation element 635 relative to the displayed nerve 622 and tongue portion 620. Moreover, the different views of the image module 602 can be displayed in combination with a graphical display (such as image 40 in FIG. 1 or the images of FIGS. 4-5) of activated muscles and stimulated nerves (as described in association with at least FIGS. 1-9), thereby providing real-time indication of the precise location of a stimulation element and the effectiveness of the stimulation element at that location for activating a target muscle.

Figure 14:
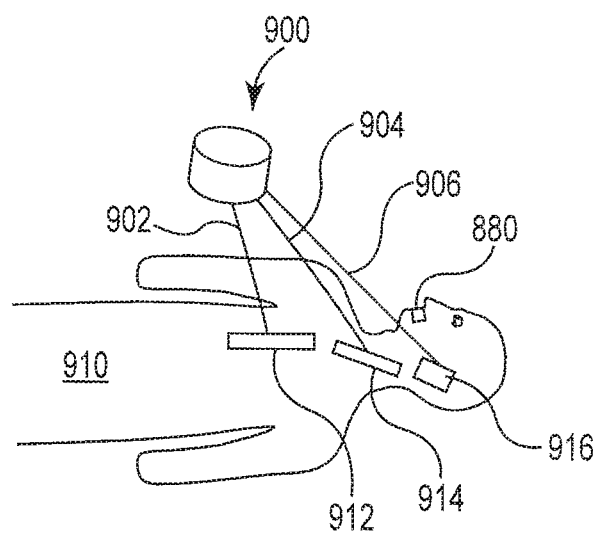
FIG. 14 is a schematic illustration an illumination system for illuminating anatomical features of a patient, according to an embodiment of the present general inventive concept.

In one embodiment, system 600 includes an array of reflectors placeable on various anatomical landmarks of a patient, on tools (and different portions of the tools), and the general environment in which the patient is situated. For example, as illustrated in FIG. 14, placement of a marker 880 on a patient's chin provides one such anatomical landmark relevant for visualizing procedures in the area of the head and neck. Using an infrared camera, the various locations of the reflectors are identified and compiled into a three-dimensional map suitable to guide navigation during an invasive procedure. In some embodiments, system 600 further includes a laser projection function 900, as illustrated in FIG. 14. Laser projection function 900 projects different colors 902, 904, 906 directly onto a patient 910 (based on the infrared anatomical reference points, other interpolated anatomical positions, and internal imaging information, as described in association with FIG. 10) to guide navigation of instruments (e.g. a test tool, a stimulation element, a percutaneous access system, a transvenous access system) on an intended navigational path 912, 914, actual navigational path, and/or intended target 916 of the navigational path, as generally illustrated in FIG. 14. In one embodiment, the differently color illumination provided via the laser projection function 900 is displayed in combination with a graphical display (such as image 40 in FIG. 1 or the images of FIGS. 4-5) of activated muscles and stimulated nerves (as described in association with at least FIGS. 1-9), thereby providing real-time indication of the precise location of a stimulation element and the effectiveness of the stimulation element at that location for activating a target muscle.

In some embodiment, the color laser projection functionality greatly facilitates a transvenous access method of delivery of the stimulation element and/or test tool, as this method does not include accessing the target nerve via surface cutting of tissue.

Figure 11:
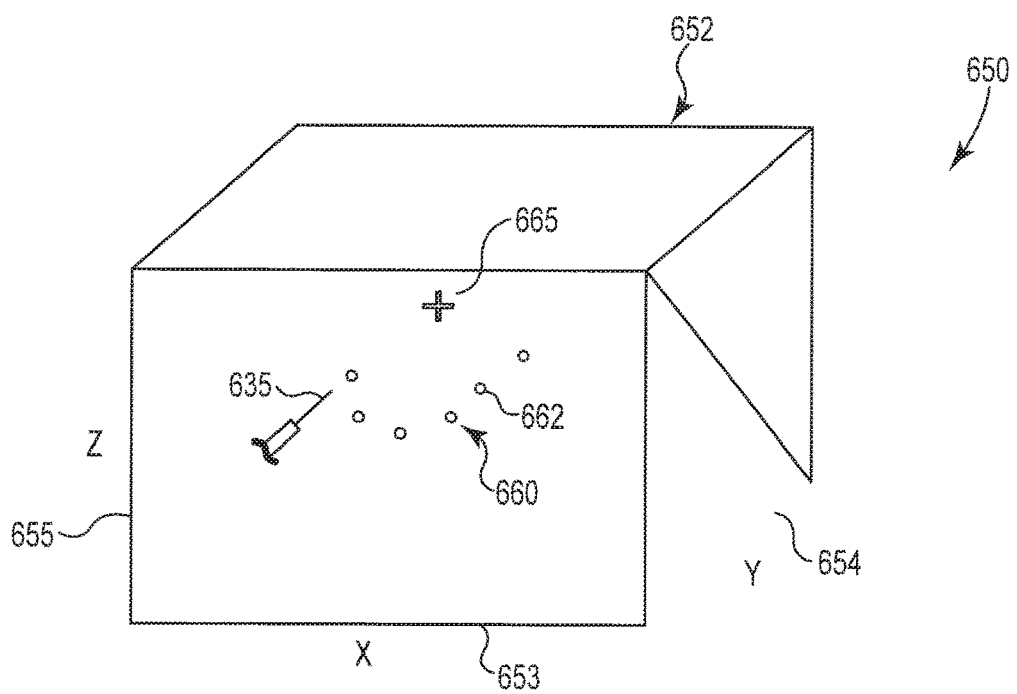
FIG. 11 schematically illustrates a system and user interface for navigating and tracking a pathway of a stimulation element, according to an embodiment of the present general inventive concept.

FIG. 11 is a schematic illustration of an image-based visualization system 600 used in a method of identifying a target stimulation location and/or navigation pathway, according to an embodiment of the present general inventive concept. As shown in FIG. 11, system 650 includes interface 652. In one embodiment, system 650 corresponds to a LocaLisa™ type non-fluoroscopic imaging system available from Medtronic of Fridley, Minn. Interface 652 provides a three-dimensional representation of a body region along three orthogonal axes 653 ($x$), 654 ($y$), 655 ($z$). Using surface mounted electrodes arranged about an outer surface of the body portion, movement of a stimulation element 635 (test tool or implantable electrode) is tracked along a path 660 of internal locations 662 using voltage and impedance information from the surface-mounted electrodes and the conductive stimulation element 635. A reference marker 665 provides an independent reference point. With this arrangement, an image is generated of a navigated path and the location of the stimulation element 635. In some embodiments, this generated image is superimposed with patient anatomy maps and more comprehensive images (e.g. MRI), as previously described in association with FIGS. 1-9, for display in interface 30, 212 (FIGS. 1,3) to assist in placing the stimulation element.

It will be understood that different combinations of the components of the image and navigation interfaces can be made, such as but not limited to, including or excluding a nerve-muscle index 294 (FIGS. 6B and 12) with an image interface 40, including or excluding a functional result module, or even including or excluding a sensor probe interface.

Embodiments of the present general inventive concept provide for dynamic real-time identification of muscle activation from electrical stimulation in context with image-based navigation tools, thereby enhancing placement of stimulation element within a body portion of a patient.

While at least one exemplary embodiment has been presented in the foregoing detailed description, it should be appreciated that variations exist. It should also be appreciated that the exemplary embodiment or exemplary embodiments are only examples, and are not intended to limit the scope, applicability, or configuration of the present general inventive concept in any way. Rather, the foregoing detailed description will provide those skilled in the art with a convenient road map for implementing the exemplary embodiment or exemplary embodiments. It should be understood that various changes can be made in the function and arrangement of elements without departing from the scope of the present general inventive concept as set forth in the appended claims and the legal equivalents thereof.

The invention claimed is:

1. A method comprising:
    identifying a target therapy stimulation site along a length of a nerve within a patient's body via:

determining, separately for each potential therapy stimulation site among a plurality of potential therapy stimulation sites along a length of a nerve, a neuromuscular response of muscles produced upon applying a stimulation signal via a stimulation test tool at the respective potential therapy stimulation sites, the stimulation test tool being separate from, and independent of, an implantable therapy stimulation electrode;

determining, based on the identified target therapy stimulation site, an access pathway to deliver the implantable therapy stimulation electrode to the identified target therapy stimulation site, wherein the determining includes visualizing in real-time, via an image-based graphical user interface, at least one internal image of the patient's body; and delivering, via the determined access pathway, the implantable therapy stimulation electrode to the identified target therapy stimulation site.

2. The method of claim 1, comprising:
performing both the determining the access pathway and the delivery of the implantable therapy stimulation electrode in a head-and-neck portion of the patients' body; and
performing the determination for the neuromuscular response in the head-and-neck portion of the patient's body.

3. The method of claim 1, comprising determining the neuromuscular response as at least one of a tongue muscle response or an upper airway response.

4. The method of claim 1, wherein at least the determining the access pathway and the delivering are performed via an image-based navigation interface.

5. The method of claim 1, wherein the access pathway comprises a percutaneous access pathway.

6. The method of claim 1, comprising:
arranging the implantable therapy stimulation electrode as a cuff electrode.

7. The method of claim 1, comprising:
locating the respective potential therapy stimulation sites at at least one of a main branch or a medial branch of the hypoglossal nerve.

8. The method of claim 1, wherein the delivery of the implantable therapy stimulation electrode comprises:
performing the delivery to exclude non-target nerve branches innervating muscles that retract the tongue and to include target nerve branches that protrude the tongue.

9. The method of claim 1, wherein the delivery of the implantable therapy stimulation electrode comprises:
performing the delivery to exclude non-target nerve branches innervating the styloglossus muscle and to include target nerve branches innervating the genioglossus muscle.

10. The method of claim 1, comprising:
further locating the respective potential therapy stimulation sites to activate at least one of a genioglossus muscle group, a geniohyoid muscle group, a styloglossus muscle group, or a hyoglossus muscle group.

11. The method of claim 1, comprising:
displaying, via the at least one internal image of the patient within the image-based graphical user interface, a location of the implantable therapy stimulation electrode within the patient body and at least one muscle group or at least one nerve to which stimulation was applied.

12. The method of claim 1, comprising at least one of:
displaying, via the at least one internal image of the patient within the image-based navigation interface, a graphic identification of which muscles were activated for each respective potential therapy stimulation site upon applying the stimulation signal via the stimulation test tool; and
displaying, via the at least one internal image of the patient within the image-based navigation interface, the graphic identification of which muscles and which nerves within the patient body which were not activated during application of the stimulation signal via the stimulation test tool.

13. The method of claim 12, comprising:
highlighting the respective potential therapy stimulation sites that correspond to the activated muscles using substantially the same visual indication that was displayed for the activated muscles.

14. The method of claim 1, wherein determining the neuromuscular response of muscles comprises:
removably coupling, prior to applying the stimulation signal, a plurality of sensor probes relative to a corresponding plurality of potentially activatable muscles, with each potentially activatable muscle being innervated by one of the respective potential therapy stimulation sites.

15. The method of claim 1, wherein determining the neuromuscular response comprises:
differentiating the cause of the neuromuscular response of an activated muscle from among the group of:
an electrical stimulation of the target nerve;
direct electrical stimulation of the activated muscle; and
motion of an activated muscle.

16. The method of claim 1, comprising performing treatment of obstructive sleep apnea via applying the stimulation signal via the implantable therapy stimulation electrode at the final placement.

* * * * *